(12) United States Patent
Pei

(10) Patent No.: US 11,673,919 B2
(45) Date of Patent: Jun. 13, 2023

(54) BICYCLIC PEPTIDYL INHIBITORS

(71) Applicant: Ohio State Innovation Foundation, Columbus, OH (US)

(72) Inventor: Dehua Pei, Columbus, OH (US)

(73) Assignee: Ohio State Innovation Foundation, Columbus, OH (US)

(*) Notice: Subject to any disclaimer, the term of this patent is extended or adjusted under 35 U.S.C. 154(b) by 0 days.

(21) Appl. No.: 17/750,966

(22) Filed: May 23, 2022

(65) Prior Publication Data

US 2022/0281920 A1 Sep. 8, 2022

Related U.S. Application Data

(62) Division of application No. 16/753,681, filed as application No. PCT/US2018/054345 on Oct. 4, 2018, now Pat. No. 11,339,192.

(60) Provisional application No. 62/568,221, filed on Oct. 4, 2017.

(51) Int. Cl.
*C07K 7/64* (2006.01)
*A61P 35/00* (2006.01)

(52) U.S. Cl.
CPC ............... *C07K 7/64* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,595,756 A | * | 1/1997 | Bally ............... A61K 9/1272 264/4.1 |
| 6,960,648 B2 | | 11/2005 | Bonny |
| 8,883,718 B2 | | 11/2014 | Warenius |
| 2002/0035243 A1 | | 3/2002 | Imfeld et al. |
| 2002/0120100 A1 | | 8/2002 | Bonny |
| 2003/0032594 A1 | | 2/2003 | Bonny |
| 2014/0342992 A1 | | 11/2014 | Gait et al. |
| 2016/0115202 A1 | | 4/2016 | Pei et al. |
| 2017/0190743 A1 | | 7/2017 | Pei et al. |
| 2017/0355730 A1 | | 12/2017 | Pei et al. |
| 2019/0282654 A1 | | 9/2019 | Pei et al. |
| 2019/0309020 A1 | | 10/2019 | Pei et al. |

FOREIGN PATENT DOCUMENTS

| | | |
|---|---|---|
| WO | 2017/109076 | 6/2017 |
| WO | 2017/147283 | 8/2017 |
| WO | 2018/098231 | 5/2018 |
| WO | 2019/217682 | 11/2019 |

OTHER PUBLICATIONS

Zugazagoitia et al, Current Challenges in Cancer Treatment, Clinical Therapies, vol. 38, (2016), pp. 1551-156 (Year: 2016).*
Sporn et at, "Chemoprevention of Cancer," Carcinogenesis, vol. 21 (2000), 525-530 (Year: 2000).*
Cardote, Teresa AF, and Alessio Ciulli. "Cyclic and macrocyclic peptides as chemical tools to recognise protein surfaces and probe protein-protein interactions." ChemMedChem 11.8 (2016): 787-794.
Chen, Ying, et al. "Inhibition of the nuclear export receptor XPO1 as a therapeutic target for platinum-resistant ovarian cancer." Clinical Cancer Research 23.6 (2017): 1552-1563.
Chen, Xianwen, et al. "On-bead screening of combinatorial libraries: reduction of nonspecific binding by decreasing surface ligand density." Journal of combinatorial chemistry 11.4 (2009): 604-611.
Chistiakov, Dimitry A., and Emma I. Chistiakova. "T-cell protein tyrosine phosphatase: A role in inflammation and autoimmunity." International Journal of Diabetes Mellites 2.2 (2010): 114-118.
Cildir, Gokhan, Kee Chung Low, and Vinay Tergaonkar. "Noncanonical NF-κB signaling in health and disease." Trends in molecular medicine 22.5 (2016): 414-429.
Dai, Simon, et al. "The IκB kinase (IKK) inhibitor, NEMO-binding domain peptide, blocks osteoclastogenesis and bone erosion in inflammatory arthritis." Journal of Biological Chemistry 279.36 (2004): 37219-37222.
Davé, Shaival H., et al. "Amelioration of chronic murine colitis by peptide-mediated transduction of the IκB kinase inhibitor NEMO binding domain peptide." The Journal of Immunology 179.11 (2007): 7852-7859.
Delfin DA, et al., "Improvement of cardiac contractile function by peptide-based inhibition of NF-κB in the utrophin/dystrophin-deficient murine model of muscular dystrophy." J Transl Med. 2011;9:68. Published May 17, 2011. doi:10.1186/1479-5876-9-68.
Dougherty, Patrick G., Ziqing Qian, and Dehua Pei. "Macrocycles as protein-protein interaction inhibitors." Biochemical Journal 474.7 (2017): 1109-1125.
Eisenberg, David, Robert M. Weiss, and Thomas C. Terwilliger. "The hydrophobic moment detects periodicity in protein hydrophobicity." Proceedings of the National Academy of Sciences 81.1 (1984): 140-144.
Elchebly, Mounib, et al. "Increased insulin sensitivity and obesity resistance in mice lacking the protein tyrosine phosphatase-1B gene." Science 283.5407 (1999): 1544-1548.

(Continued)

*Primary Examiner* — Thomas S Heard
(74) *Attorney, Agent, or Firm* — Meunier Carlin & Curfman LLC

(57) ABSTRACT

The present disclosure provides a large combinatorial library of cell-permeable bicyclic peptides. The bicyclic peptides described herein include the first ring consisted of randomized peptide sequences for potential binding to a target of interest while the second ring featured a family of different cell-penetrating motifs, for both cell penetration and target binding. The library was screened against the IκB kinase α/β (IKKα/β)-binding domain of NF-κB essential modulator (NEMO), resulting in the discovery of several cell-permeable bicyclic peptides which inhibited the NEMO-IKKβ interaction, thereby selectively inhibiting canonical NF-κB signaling in mammalian cells and the proliferation of cisplatin-resistant ovarian cancer cells.

14 Claims, 5 Drawing Sheets

Figure 1:
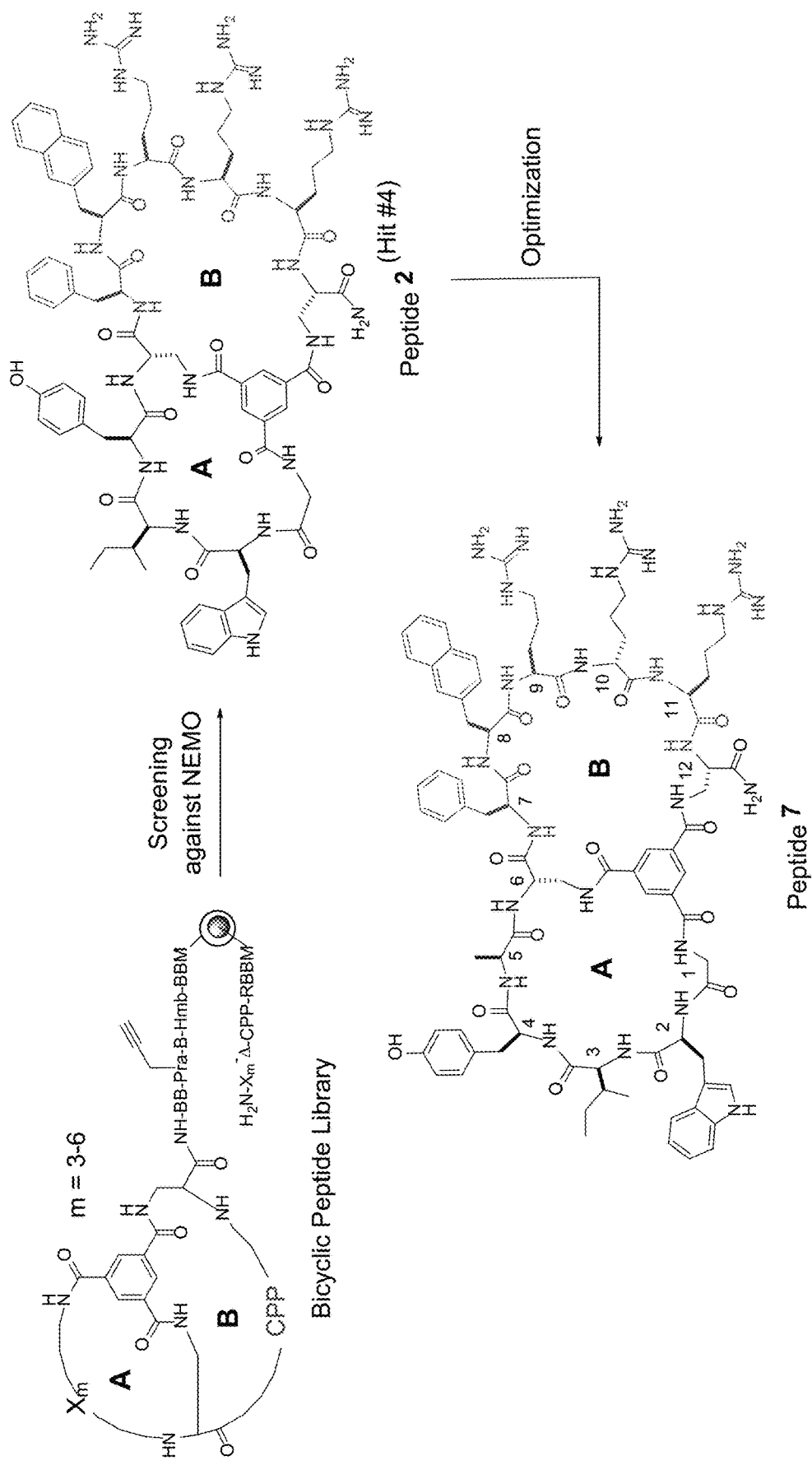

Specification includes a Sequence Listing.

(56) References Cited

OTHER PUBLICATIONS

Engleman, et al. Ann. Rev. of Biophys. Biophys. Chem. 1986, 15):321-53.
Gaurnier-Hausser, Anita, et al. "NEMO-binding domain peptide inhibits constitutive NF-κB activity and reduces tumor burden in a canine model of relapsed, refractory diffuse large B-cell lymphoma." Clinical Cancer Research 17.14 (2011): 4661-4671.
Godwin, Peter, et al. "Targeting nuclear factor-kappa B to overcome resistance to chemotherapy." Frontiers in oncology 3 (2013): 120.
Gotoh, Yusuke, et al. "A homogeneous time-resolved fluorescence-based high-throughput screening system for discovery of inhibitors of IKKβ-NEMO interaction." Analytical biochemistry 405.1 (2010): 19-27.
Guo, Bingqian, et al. "Protein engineering of the N-terminus of NEMO: Structure stabilization and rescue of IKKβ binding." Biochemistry 53.43 (2014): 6776-6785.
Gupta, Subash C., et al. "Inhibiting NF-κB activation by small molecules as a therapeutic strategy." Biochimica et Biophysica Acta (BBA)-Gene Regulatory Mechanisms 1799.10-12 (2010): 775-787.
Ndikuyeze, Georges Habineza, et al. "A phase I clinical trial of systemically delivered NEMO binding domain peptide in dogs with spontaneous activated B-cell like diffuse large B-cell lymphoma." PloS one 9.5 (2014): e95404.
Hernandez, Lídia, et al. "Activation of NF-κB signaling by inhibitor of NF-κB kinase β increases aggressiveness of ovarian cancer." Cancer research 70.10 (2010): 4005-4014.
Herndon, Thomas M., et al. "US Food and Drug Administration approval: carfilzomib for the treatment of multiple myeloma." Clinical cancer research 19.17 (2013): 4559-4563.
Herrington, Felicity D., Ruaidhri J. Carmody, and Carl S. Goodyear. "Modulation of NF-κB signaling as a therapeutic target in autoimmunity." Journal of biomolecular screening 21.3 (2016): 223-242.
Hopp, Thomas P., and Kenneth R. Woods. "Prediction of protein antigenic determinants from amino acid sequences." Proceedings of the National Academy of Sciences 78.6 (1981): 3824-3828.
Ianaro, Angela, et al. "NEMO-binding domain peptide inhibits proliferation of human melanoma cells." Cancer letters 274.2 (2009): 331-336.
Janin, J. O. E. L. "Surface and inside volumes in globular proteins." Nature 277.5696 (1979): 491-492.
Jiang, Bisheng, and Dehua Pei. "A selective, cell-permeable nonphosphorylated bicyclic peptidyl inhibitor against peptidyl-prolyl isomerase Pin1." Journal of medicinal chemistry 58.15 (2015): 6306-6312.
Jimi, Eijiro, et al. "Selective inhibition of NF-κB blocks osteoclastogenesis and prevents inflammatory bone destruction in vivo." Nature medicine 10.6 (2004): 617-624.
Joo, Sang Hoon, et al. "High-throughput sequence determination of cyclic peptide library members by partial Edman degradation/mass spectrometry." Journal of the American Chemical Society 128.39 (2006): 13000-13009.
Karin, Michael. "Nuclear factor-κB in cancer development and progression." Nature 441.7092 (2006): 431-436.
Kornegay, Joe N., et al. "NBD delivery improves the disease phenotype of the golden retriever model of Duchenne muscular dystrophy." Skeletal muscle 4.1 (2014): 1-17.
Kyte, Jack, and Russell F. Doolittle. "A simple method for displaying the hydropathic character of a protein." Journal of molecular biology 157.1 (1982): 105-132.
Lian, Wenlong, et al. "Screening bicyclic peptide libraries for protein-protein interaction inhibitors: discovery of a tumor necrosis factor-α antagonist." Journal of the American Chemical Society 135.32 (2013): 11990-11995.
Lian, Wenlong, et al. "Cell-permeable bicyclic peptide inhibitors against intracellular proteins." Journal of the American Chemical Society 136.28 (2014): 9830-9833.

May, F. D'Acquisto, L. A. Madge, J. Glockner, J. S. Pober, S. Ghosh, Science 2000, 289, 1550.
Morrison, Kim L., and Gregory A. Weiss. "Combinatorial alanine-scanning." Current opinion in chemical biology 5.3 (2001): 302-307.
Oeckinghaus, Andrea, and Sankar Ghosh. "The NF-κB family of transcription factors and its regulation." Cold Spring Harbor perspectives in biology 1.4 (2009): a000034.
Passioura, Toby, et al. "Selection-based discovery of druglike macrocyclic peptides." Annual review of biochemistry 83 (2014): 727-752.
Peterson, Jennifer M., et al. "Peptide-based inhibition of NF-κB rescues diaphragm muscle contractile dysfunction in a murine model of Duchenne muscular dystrophy." Molecular Medicine 17.5 (2011): 508-515.
Qian, et al., "Enhancing the Cell Permeability and Metabolic Stability of Peptidyl Drugs by Reversible Bicyclization", Angew. Chem. Int. Ed. 2017, 56, 1525-1529.
Qian, Ziqing, et al. "Early endosomal escape of a cyclic cell-penetrating peptide allows effective cytosolic cargo delivery." Biochemistry 53.24 (2014): 4034-4046.
Qian, Ziqing, et al. "Discovery and mechanism of highly efficient cyclic cell-penetrating peptides." Biochemistry 55.18 (2016): 2601-2612.
Reay, M. Yang, J. F. Watchko, M. Daood, T. L. O'Day, K. K. Rehman, D. C. Guttridge, P. D. Robbins, P. R. Clemens, Neurobiol. Dis. 2011, 43, 598.
Rothwarf, David M., et al. "IKK-γ is an essential regulatory subunit of the IκB kinase complex." Nature 395.6699 (1998): 297-300.
Rushe, Mia, et al. "Structure of a NEMO/IKK-associating domain reveals architecture of the interaction site." Structure 16.5 (2008): 798-808.
Shibata, Wataru, et al. "Cutting edge: the IκB kinase (IKK) inhibitor, NEMO-binding domain peptide, blocks inflammatory injury in murine colitis." The Journal of Immunology 179.5 (2007): 2681-2685.
Shrake, Andrew, and John A. Rupley. "Environment and exposure to solvent of protein atoms. Lysozyme and insulin." Journal of molecular biology 79.2 (1973): 351-371.
Sun, Shao-Cong, Jae-Hoon Chang, and Jin Jin. "Regulation of nuclear factor-κB in autoimmunity." Trends in immunology 34.6 (2013): 282-289.
Thakkar, Amit, Anne-Sophie Wavreille, and Dehua Pei. "Traceless capping agent for peptide sequencing by partial Edman degradation and mass spectrometry." Analytical chemistry 78.16 (2006): 5935-5939.
Tien, Matthew Z., et al. "Maximum allowed solvent accessibilites of residues in proteins." PloS one 8.11 (2013): e80635.
Trinh, Thi B., et al. "Discovery of a direct Ras inhibitor by screening a combinatorial library of cell-permeable bicyclic peptides." ACS combinatorial science 18.1 (2016): 75-85.
Upadhyaya, Punit, et al. "Inhibition of Ras signaling by blocking Ras-effector interactions with cyclic peptides." Angewandte Chemie International Edition 54.26 (2015): 7602-7606.
Verma, Udit N., et al. "Nuclear role of IκB kinase-γ/NF-κB essential modulator (IKKγ/NEMO) in NF-κB-dependent gene expression." Journal of Biological Chemistry 279.5 (2004): 3509-3515.
Yamaoka, Shoji, et al. "Complementation cloning of NEMO, a component of the IκB kinase complex essential for NF-κB activation." Cell 93.7 (1998): 1231-1240.
Zhang, Zhong-Yin. "Drugging the undruggable: therapeutic potential of targeting protein tyrosine phosphatases." Accounts of chemical research 50.1 (2017): 122-129.
Zhang, Sheng, et al. "Acquisition of a potent and selective TC-PTP inhibitor via a stepwise fluorophore-tagged combinatorial synthesis and screening strategy." Journal of the American Chemical Society 131.36 (2009): 13072-13079.

* cited by examiner

BICYCLIC PEPTIDYL INHIBITORS

CROSS-REFERENCE TO RELATED APPLICATIONS

This application is a divisional application of U.S. application Ser. No. 16/753,681, filed Apr. 3, 2020, which is a national stage application filed under 35 U.S.C. § 371 of PCT/US2018/054345 filed Oct. 4, 2018, which claims the benefit of U.S. Provisional Application No. 62/568,221, filed on Oct. 4, 2017, which is incorporated by reference herein in its entirety.

ACKNOWLEDGMENT OF GOVERNMENT SUPPORT

This invention was made with government support under GM110208, GM122459, and GM008512 awarded by the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CYPT_008_01US_SubSeqList_ST25.txt, date recorded: Aug. 4, 2021, file size ~52.1 kilobytes).

BACKGROUND

Protein-protein interaction (PPI) is a fundamental aspect of biological processes, and such interactions mediate numerous disease. However, intracellular PPIs are challenging targets for current drug modalities (i.e., small molecules and biologics) and represent the largest untapped opportunity for therapeutic development.

NF-κB essential modulator (NEMO) is a regulatory protein of the canonical NF-κB signaling pathway. During canonical NF-κB signaling, receptor activation at the cell surface results in the formation of an active inhibitor of κB (IκB)-kinase (IKK) complex consisting of IKKα, IKKβ, and NEMO (which is also called IKKγ). Aberrant activation of the canonical pathway is implicated in many inflammatory and autoimmune diseases, as well as cancer.

The NEMO-IKK complex has been a challenging target for drug discovery. Small molecule inhibitors do not display high enough potency against the NEMO-IKK interaction to be a viable therapeutic strategy. Therefore, there is still need for developing potent peptidyl inhibitors of the NEMO-IKK interaction as a novel class of anti-inflammatory and anti-cancer drugs.

BRIEF DESCRIPTIONS OF THE FIGURES

FIG. 1 depicts structures of the bicyclic peptide library, hit No. 4, and peptide 7. Amino acid residues in peptide 7 are numbered from N- to C-terminus. The CPP sequence is shown in red, whereas the residues modified during optimization are shown in blue color. B, β-alanine; CPP, cell-penetrating peptide; Hmb, hydroxylmethylbenzoyl; Pra, propargylglycine; Δ, L-2,3-diaminopropionic acid (Dap).

Figure 2A:
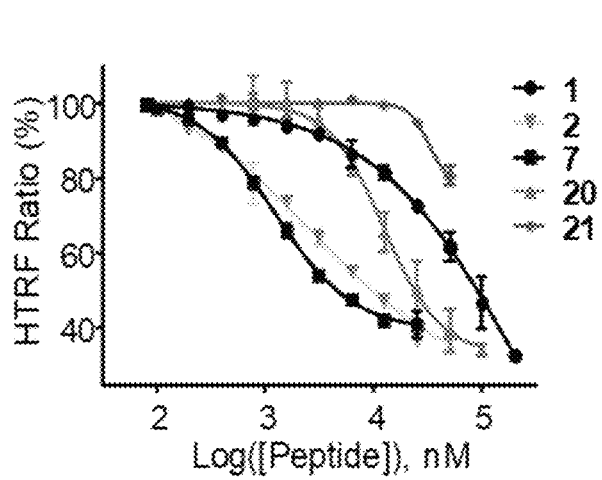
Figure 2B:
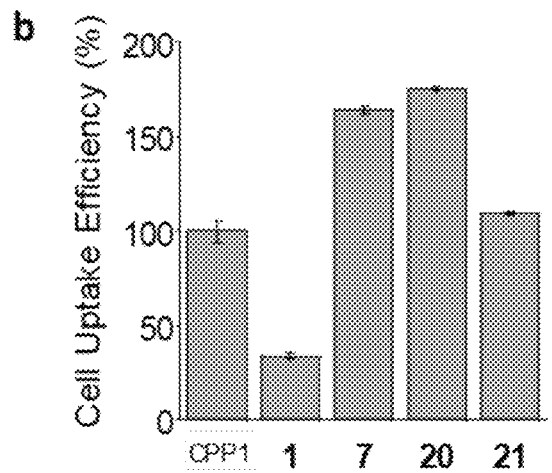
Figure 2C:
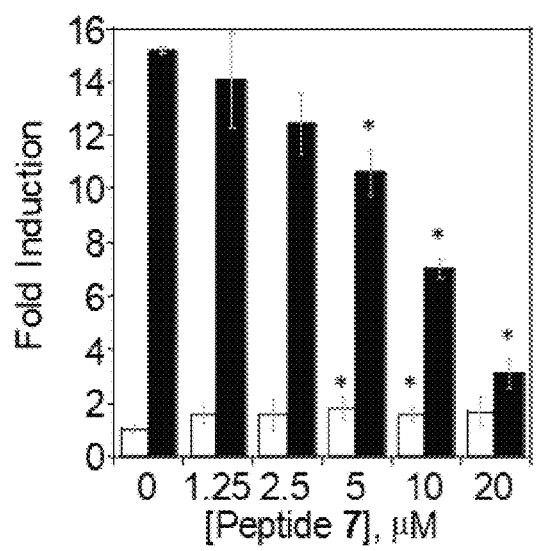
Figure 2D:
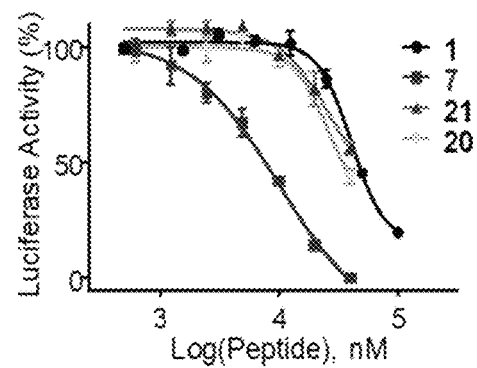
Figure 2E:
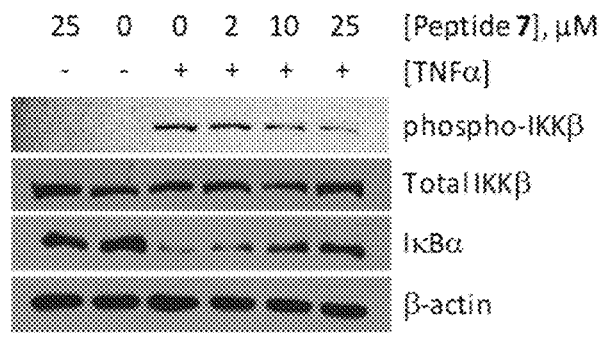

FIGS. 2A-2E illustrate the inhibition of the NEMO-IKK$_{\alpha/\beta}$ interaction and NF-κB signaling by peptide 7 and control peptides. FIG. 2A shows the inhibition of the NEMO-IKKβ interaction as monitored by the HTRF assay. FIG. 2B shows the cellular uptake efficiency of FITC-labeled peptides into HeLa cells as determined by flow cytometry. All values are relative to that of CPP1 (100%). FIG. 2C shows differential effects of pep-tide 7 on the basal (open bars) and TNFα-induced NF-κB activation (closed bars) in HEK293(Luc) cells. *, $p<0.001$ using Student's t-test. FIG. 2D compares peptides 1, 7, 20, and 21 for inhibition of TNFα-induced luciferase activity in HEK293 (Luc) cells. FIG. 2E is a western blot showing the effect of peptide 7 on IκBα and IKKβ levels in HT29 colon cancer cells in the absence and presence of TNFα.

Figures 3A, 3B, 3C:
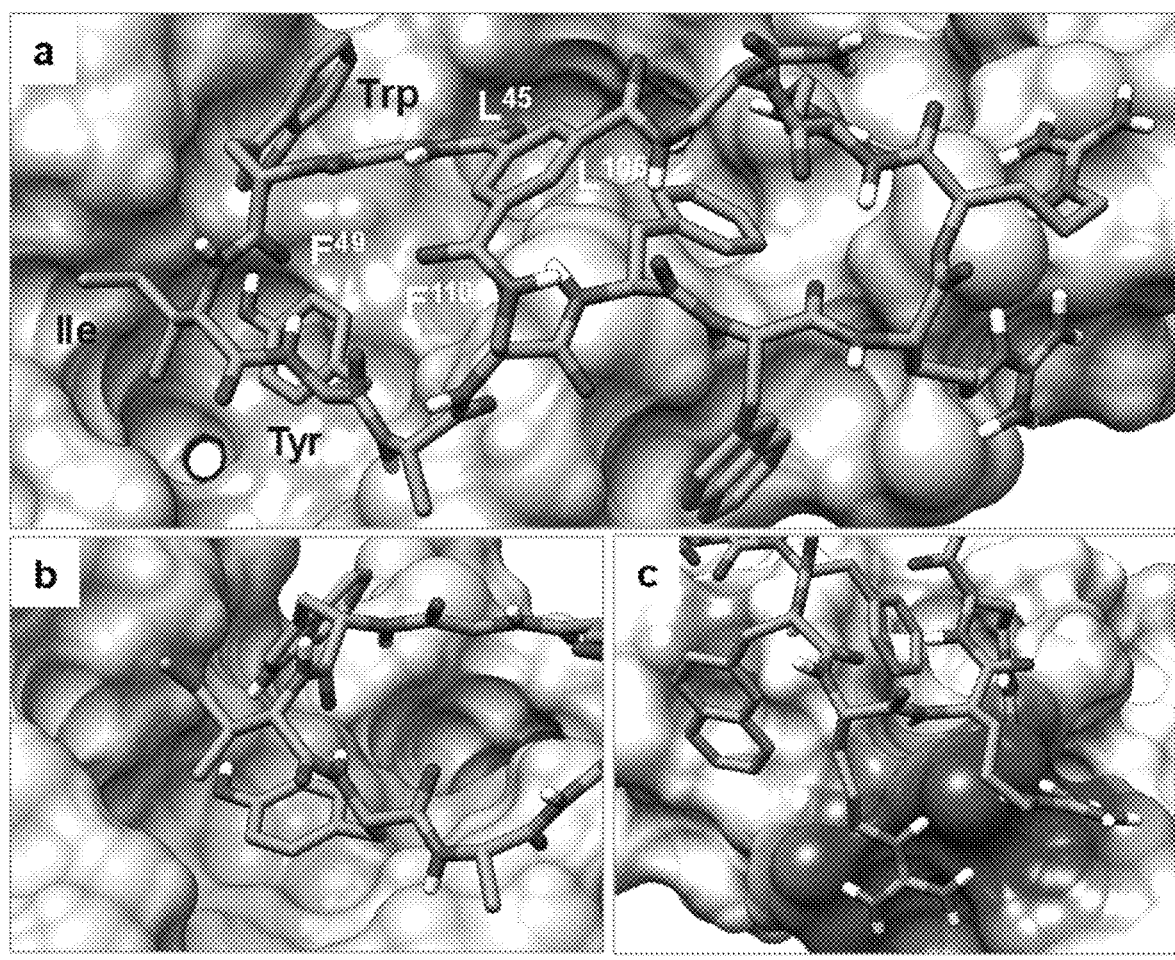

FIGS. 3A-3C show in silico model of the NEMO-peptide 7 complex. FIG. 3A shows the overall complex between peptide 7 (shown as green sticks) and NEMO (PDBID: 3BRT; shown as van der Waals surface) with residues critical for the NEMO-IKKβ interaction shaded pink. FIG. 3B is a close-up of the interaction between the A ring (in green) and NEMO including the insertion of Tyr-4 into a hydrophobic pocket. FIG. 3C shows a zoom-in view of the charge-charge interactions between the three arginine residues of peptide 7 and acidic residues on NEMO. Basic and acidic residues of NEMO are shown in blue and red, respectively.

Figure 4A:
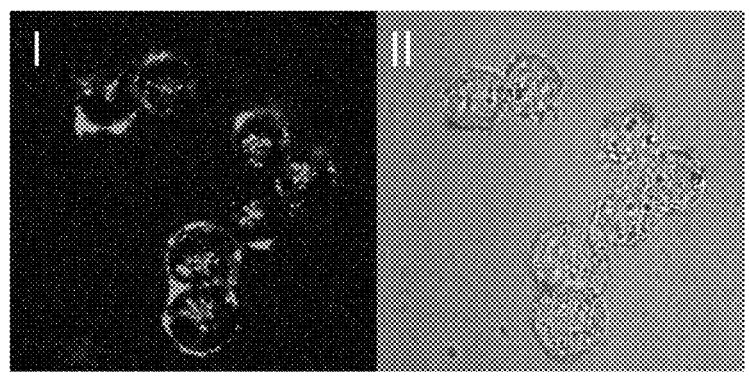
Figure 4B:
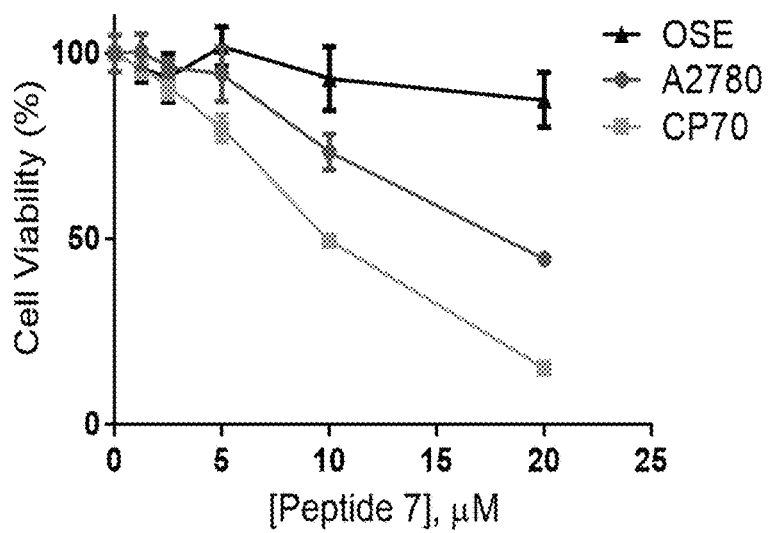
Figure 4C:
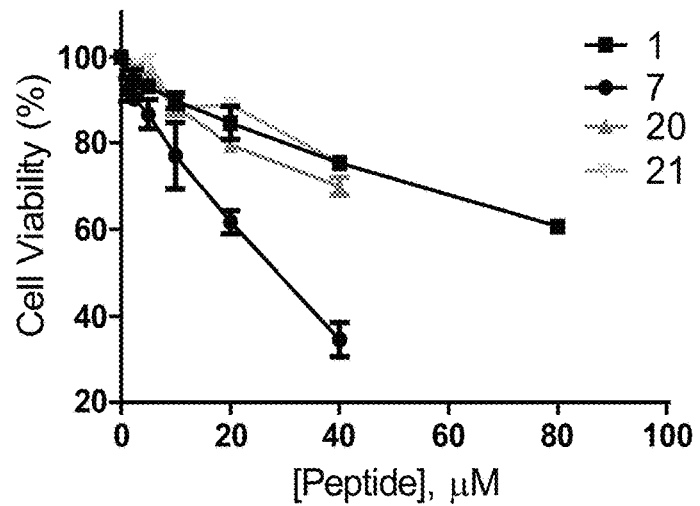
Figure 4D:
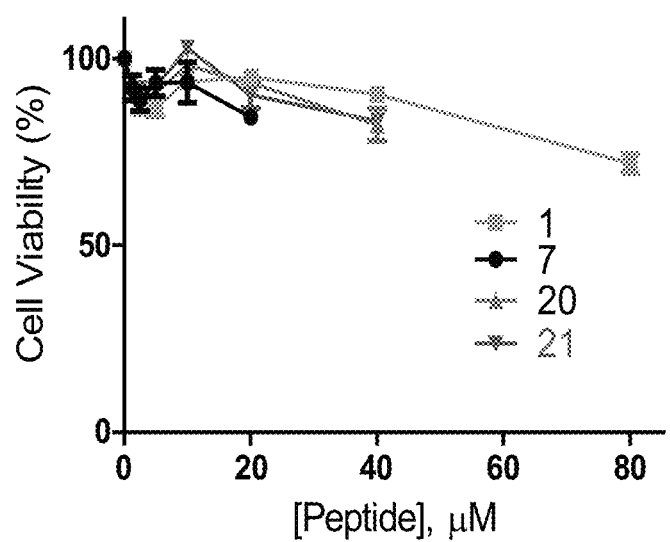

FIGS. 4A-4D show the anticancer activity of peptide 7. FIG. 4A shows live-cell confocal microscopic image of A2780 ovarian cancer cells after 2-hour treatment with 5 μM FITC-peptide 7. I, FITC fluorescence; II, DIC. FIG. 4B shows viability of ovarian cancer cells (A2780 and CP70) and non-cancerous ovarian cells (OSE) in the presence of increasing concentrations of peptide 7, as determined by the methylene blue assay. FIG. 4C compares peptide 7 and control peptides for their effect on the viability of A2780 cells. FIG. 4D shows the effect of peptide 7 and control peptides on non-cancerous OSE cells. Viability tests in panel (c) and (d) were performed by the MTT assay.

DETAILED DESCRIPTION

Bicyclic Polypeptides

Disclosed herein, in various embodiments, are bicyclic polypeptides. The bicyclic polypeptides have a first polypeptide sequence which forms a first ring (referred to herein as the "A ring"), and a second polypeptide sequence which forms a second ring (referred to herein as the "B ring"). In some embodiments, the bicyclic polypeptides disclosed herein penetrate the cell membrane and are capable of inhibiting intracellular protein-protein interactions.

In some embodiments, the bicyclic polypeptides comprise a first sequence which is capable of inhibiting a protein-protein interaction (referred to herein as the "Xm" sequence), and a second sequence which is capable of penetrating a cell membrane (referred to herein as the "CPP" sequence). In various embodiments, the Xm sequence may include amino acids which influence or participate in cellular penetration. Similarly, in embodiments, the CPP sequence may include amino acids which participate in inhibiting a protein-protein interaction.

In various embodiments, the disclosure provides for bicyclic polypeptides according to Formula 1A or 1B:

(1A)

-continued

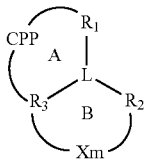
(1B)

wherein:
CPP is a cell-penetrating peptide sequence;
Xm is a peptide sequence that binds to a NF-κB essential modulator (NEMO) protein;
L is a linker moiety; and
each of $R_1$, $R_2$, and $R_3$ are, independently, a bonding moiety,
wherein the bonding moiety is formed when Xm, CPP, or a combination thereof, covalently bind to L to form the bicyclic polypeptide.

In various embodiments, the disclosure provides for bicyclic polypeptides according to Formula 1C or 1D:

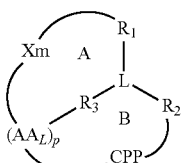
(1C)

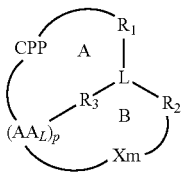
(1D)

wherein:
CPP is a cell-penetrating peptide sequence;
Xm is a peptide sequence that binds to a NF-κB essential modulator (NEMO) protein;
$AA_L$ at each instance is an amino acid;
p is selected from a number from 0 to 3 (e.g., 0, 1, 2, or 3);
L is a linker moiety; and
each of $R_1$, $R_2$, and $R_3$ are independently, a bonding moiety,
wherein the bonding moiety is formed when Xm, CPP, $AA_L$ or a combination thereof, covalently bind to L to form the bicyclic polypeptide.

Non-limiting examples of bicyclic polypeptides of the present disclosure are provided in Example 1.

Xm Sequence

As discussed above, the bicyclic polypeptides disclosed herein comprise a sequence which is capable of binding to a NEMO protein ("Xm"). In further embodiments, the Xm sequence binds the IKKα/β-binding domain on NEMO. In such embodiments, the Xm sequence can be an appropriate combination of amino acids that binds to IKKα/β-binding domain on NEMO Suitable amino acid sequences in the Xm sequence for use in the bicyclic polypeptides and methods described herein can include naturally occurring sequences, modified sequences, and synthetic sequences. In embodiments, the total number of amino acids in the Xm may be in the range of from 3 to about 20 amino acids, e.g., about 4, about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the Xm disclosed herein comprise about 4 to about to about 13 amino acids. In particular embodiments, the Xm disclosed herein comprise about 4 to about 10 amino acids, or about 4 to about 8 amino acids. In other particular embodiments, the Xm disclosed herein comprise about 6 amino acids.

Each amino acid in the Xm may be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| alanine | Ala (A) | ala (a) |
| allosoleucine | AIle | aile |
| arginine | Arg (R) | arg (r) |
| asparagine | Asn (N) | asn (n) |
| aspartic acid | Asp (D) | asp (d) |
| cysteine | Cys (C) | cys (c) |
| cyclohexylalanine | Cha | cha |
| 2,3-diaminopropionic acid | Dap | dap |
| 4-fluorophenylalanine | Fpa (Σ) | fpa |
| glutamic acid | Glu (E) | glu (e) |
| glutamine | Gln (Q) | gln (q) |
| glycine | Gly (G) | gly (g) |
| histidine | His (H) | his (h) |
| homoproline (aka pipecolic acid) | Pip (Θ) | pip (⊖) |
| isoleucine | Ile (I) | ile (i) |
| leucine | Leu (L) | leu (l) |
| lysine | Lys (K) | lys (k) |
| methionine | Met (M) | met (m) |
| napthylalanine | Nal (Φ) | nal (φ) |
| norleucine | Nle (Ω) | nle |
| phenylalanine | Phe (F) | phe (F) |
| phenylglycine | Phg (Ψ) | phg |
| 4-(phosphonodifluoromethyl) phenylalanine | $F_2$Pmp (Λ) | $f_2$pmp |
| proline | Pro (P) | pro (p) |
| sarcosine | Sar (Ξ) | sar |
| selenocysteine | Sec (U) | sec (u) |
| serine | Ser (S) | ser (s) |
| threonine | Thr (T) | thr (y) |
| tyrosine | Tyr (Y) | tyr (y) |
| tryptophan | Trp (W) | trp (w) |
| valine | Val (V) | val (v) |

*single letter abbreviations: when shown in capital letters herein it indicates the L-amino acid form, when shown in lower case herein it indicates the D-amino acid form.

In particular embodiments, the Xm sequence includes one or more amino acids selected from G, g, W, w, I, i, Y, y, A, and a. In certain embodiments Xm is a 3-7 amino acid sequence comprising at least one W or w. In certain embodiments Xm is a 3-7 amino acid sequence comprising at least one I or i. In certain embodiments Xm is a 3-7 amino acid sequence comprising a sequence selected from WI, IW, Wi, iW, wI, Iw, iw, wi. In certain embodiments Xm is a 3-7 amino acid sequence comprising WI. In further embodiments, the Xm is a 4-7 amino acid sequence comprising a sequence selected from the group consisting of: GWIY (SEQ ID NO:1); GWIYA (SEQ ID NO:2); GWIYa (SEQ ID NO:50); AGWIY (SEQ ID NO:3); aGWIY (SEQ ID NO:51); AWIYA (SEQ ID NO:4); GAIYA (SEQ ID NO:5); GWAYA (SEQ ID NO:6); GWIAA (SEQ ID NO:7); GWIYA (SEQ ID NO:8); GAIAA (SEQ ID NO:9); and GAAAA (SEQ ID NO:10), and the inverse of such sequences (SEQ ID NOs: 52-63).

Cell-Penetrating Peptide Sequence

As discussed above, the bicyclic polypeptides disclosed herein comprise a cell penetrating peptide sequence ("CPP"). The CPP includes any amino sequence which facilitates cellular uptake of the polypeptide conjugates disclosed herein.

In some embodiments, the CPPs may include any combination of at least two arginines and at least two hydrophobic amino acids.

In some embodiments, the CPP used in polypeptide conjugates described herein has a structure comprising Formula 2:

$$(AAu)m\text{-}AA_1\text{-}AA_2\text{-}AA_3\text{-}AA_4\text{-}(AAz)n \qquad 2$$

wherein:
each of $AA_1$, $AA_2$, $AA_3$, and $AA_4$, are independently selected from a D or L amino acid,
each of $AA_u$, and $AA_z$, at each instance and when present, are independently selected from a D or L amino acid, and
m and n are independently selected from a number from 0 to 6; and
wherein:
at least two of $AA_u$, when present, $AA_1$, $AA_2$, $AA_3$, $AA_4$, and $AA_z$, when present, are independently arginine, and
at least two of $AA_u$, when present, $AA_1$, $AA_2$, $AA_3$, $AA_4$, and $AA_z$, when present, are independently a hydrophobic amino acid.

(i) In some embodiments, each hydrophobic amino acid is independently selected from is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzyl serine, 3-(4-(benzyloxy)phenyl)-al anine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. The structures of certain of these non-natural aromatic hydrophobic amino acids (prior to incorporation into the peptides disclosed herein) are provided below. In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents.

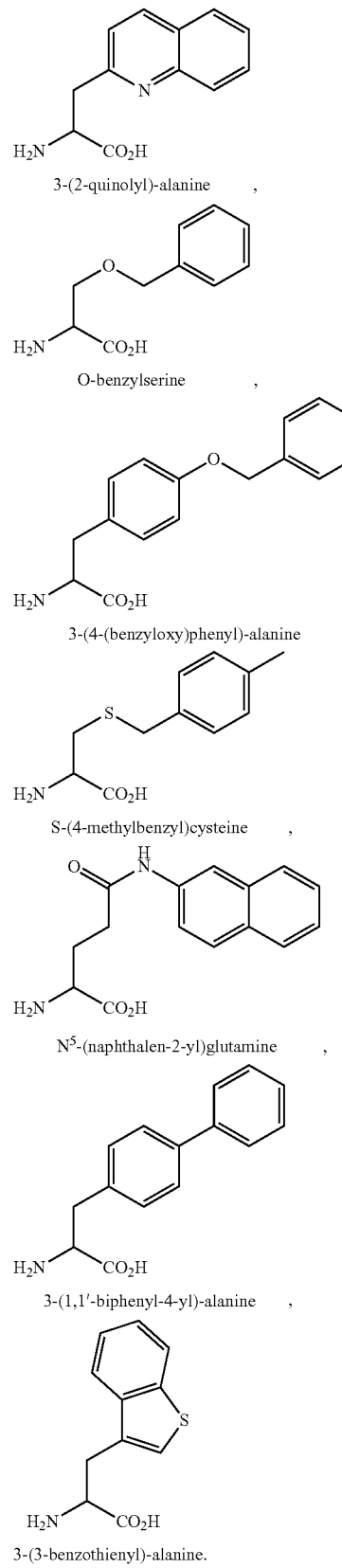

In particular embodiments, the hydrophobic amino acid is piperidine-2-carboxylic acid, naphthylalanine, tryptophan, or phenylalanine, each of which is optionally substituted with one or more substituents.

The optional substituent can be any atom or group which does not significantly reduce the cytosolic delivery efficiency of the CPP, e.g., a substituent that does not reduce relative cytosolic delivery efficiency to less than that of c(FΦRRRRQ) (SEQ ID NO: 65). In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a CPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 2

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality.

In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the CPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the CPPs described herein comprise at least two consecutive hydrophobic amino acids and at least two consecutive arginines. In further embodiments, one hydrophobic amino acid is adjacent to one of the arginines. In still other embodiments, the CPPs described herein comprise at least three consecutive hydrophobic amino acids and there consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the CPPs described herein (e.g., the CPPs according to Formula 2) can have one of the following sequences: $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid. Accordingly, in some embodiments, the CPPs used in the polypeptide conjugates described herein have a structure according any of Formula 3A-D:

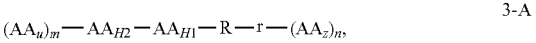
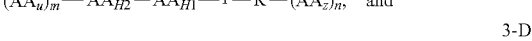

wherein:
each of $AA_{H1}$ and $AA_{H2}$ are independently a hydrophobic amino acid;
at each instance and when present, each of $AA_U$ and $AA_Z$ are independently any amino acid; and
m and n are independently selected from a number from 0 to 6.

In some embodiments, the total number of amino acids (including r, R, $AA_{H1}$, $AA_{H2}$), in the CPPs of Formula 3-A to 3-D are in the range of 4 to 10, e.g., 6. In some embodiments, the total number of amino acids is 4. In some embodiments, the total number of amino acids is 5. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments, the sum of m and n is from 2 to 6. In some embodiments, the sum of m and n is 2. In some embodiments, the sum of m and n is 3. In some embodiments, the sum of m and n is 4. In some embodiments, the sum of m and n is 5. In some embodiments, the sum of m and n is 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, or norleucine, each of which is optionally substituted with one or more substituents. In particular embodiments, each hydrophobic amino acid is independently a hydrophobic aromatic amino acid. In some embodiments, the aromatic hydrophobic amino acid is piperidine-2-carboxylic acid, naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

In some embodiments, each of $AA_{H1}$ and $AA_{H2}$ are independently a hydrophobic amino acid having a hydrophobicity value which is greater than that of glycine. In other embodiments, each of $AA_{H1}$ and $AA_{H2}$ are independently a hydrophobic amino acid having a hydrophobicity value which is greater than that of alanine. In still other embodiments, each of $AA_{H1}$ and $AA_{H2}$ are independently an hydrophobic amino acid having a hydrophobicity value which is greater than that of phenylalanine, e.g., as measured using the hydrophobicity scales described above, including Eisenberg and Weiss (Proc. Natl. Acad. Sci. U.S.A 1984; 81(1): 140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also found to improve the cytosolic uptake of the CPP (and the attached cargo). For example, in some embodiments, the CPPs disclosed herein may include $AA_{H1}$-D-Arg or D-Arg-$AA_{H1}$. In other embodiments, the CPPs disclosed herein may include $AA_{H1}$-L-Arg or L-Arg-$AA_{H1}$. In some embodiments, the presence of the hydrophobic amino acid on the N- or C-terminal of the D-Arg or L-Arg, or a combination thereof, in the CPP improves the cytosolic delivery efficiency by about 1.1 fold to about 30 fold, compared to an otherwise identical sequence, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween. In some embodiments, the presence of the hydrophobic amino acid on the N- and/or C-terminal of the D-Arg and/or L-Arg in the CPP improves the cytosolic uptake efficiency by about 20 fold.

The size of the hydrophobic amino acid on the N- or C-terminal of the D-Arg or an L-Arg, or a combination thereof (i.e., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 $Å^2$, at least about 210 Å2, at least about 220 $Å^2$, at least about 240 $Å^2$, at least about 250 $Å^2$, at least about 260 $Å^2$, at least about 270 $Å^2$, at least about 280 $Å^2$, at least about 290 $Å^2$, at least about 300 $Å^2$, at least about 310 $Å^2$, at least about 320 $Å^2$, or at least about 330 $Å^2$. In some embodiments, $AAH_2$ has a side chain side with a SASA of at least about 200 $Å^2$, at least about 210 Å2, at least about 220 $Å^2$, at least about 240 $Å^2$, at least about 250 $Å^2$, at least about 260 $Å^2$, at least about 270 $Å^2$, at least about 280 $Å^2$, at least about 290 $Å^2$, at least about 300 $Å^2$, at least about 310 $Å^2$, at least about 320 $Å^2$, or at least about 330 $Å^2$. In some embodiments, the side chains of $AAH_1$ and $AAH_2$ have a combined SASA of at least about 350 $Å^2$, at least about 360 $Å^2$, at least about 370 $Å^2$, at least about 380 $Å_2$, at least about 390 $Å^2$, at least about 400 $Å^2$, at least about 410 $Å^2$, at least about 420 $Å^2$, at least about 430 $Å^2$, at least about 440 $Å^2$, at least about 450 $Å^2$, at least about 460 $Å^2$, at least about 470 $Å^2$, at least about 480 $Å^2$, at least about 490 $Å^2$, greater than about 500 $Å^2$, at least about 510 $Å^2$, at least about 520 $Å^2$, at least about 530 $Å^2$, at least about 540 $Å^2$, at least about 550 $Å^2$, at least about 560 $Å^2$, at least about 570 $Å^2$, at least about 580 $Å^2$, at least about 590 $Å^2$, at least about 600 $Å^2$, at least about 610 $Å^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, $AA_{H2}$ is a hydrophobic amino acid with a side chain having a SASA that is less than or equal to the SASA of the hydrophobic side chain of $AA_{H1}$. By way of example, and not by limitation, a CPP having a Nal-Arg motif exhibits improved cytosolic delivery efficiency compared to an otherwise identical CPP having a Phe-Arg motif; a CPP having a Phe-Nal-Arg motif exhibits improved cytosolic delivery efficiency compared to an otherwise identical CPP having a Nal-Phe-Arg motif; and a phe-Nal-Arg motif exhibits improved cytosolic delivery efficiency compared to an otherwise identical CPP having a nal-Phe-Arg motif.

As used herein, "hydrophobic surface area" or "SASA" refers to the surface area (reported as square Angstroms; Å$^2$) of an amino acid side chain that is accessible to a solvent. In particular embodiments, SASA is calculated using the 'rolling ball' algorithm developed by Shrake & Rupley (*J Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al. (PLOS ONE 8(11): e80635. https://doi.org/10.1371/journal.pone.0080635, which is herein incorporated by reference in its entirety for all purposes.

TABLE 3

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the CPP does not include a hydrophobic amino acid on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the CPP does not include a hydrophobic amino acid having a side chain which is larger (as described herein) than at least one of $AA_{H1}$ or $AA_{H2}$. In further embodiments, the CPP does not include a hydrophobic amino acid with a side chain having a surface area greater than $AA_{H1}$. For example, in embodiments in which at least one of $AA_{H1}$ or $AA_{H2}$ is phenylalanine, the CPP does not further include a naphtylalanine (although the CPP include at least one hydrophobic amino acid which is smaller than $AA_{H1}$ and $AA_{H2}$, e.g., leucine). In still other embodiments, the CPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the CPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the CPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_H$ can be D-nal, D-trp, or D-phe. In another non-limiting example, when arginine is L-Arg, $AA_H$ can be L-Nal, L-Trp, or L-Phe.

In some embodiments, the CPPs described herein include three arginines. Accordingly, in some embodiments, the CPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R-R, $AA_{H2}$-$AA_{H1}$-r-R-r, R-R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the CPPs have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AAH_1$ and $AAH_2$ can be selected to improve cytosolic uptake efficiency, e.g., as described above, where $AAH_1$ has the same chirality as the adjacent arginine, and $AAH_1$ and $AAH_2$ have the opposite chirality.

In some embodiments, the CPPs described herein include three hydrophobic amino acids. Accordingly, in some embodiments, the CPPs described herein include one of the following sequences: $AA_{H3}$-$AA_{H2}$-$AA_{H1}$-R-r, $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, r-R-$AA_{H1}$-$AA_{H2}$-$AA_{H3}$, wherein $AA_{H3}$ is any hydrophobic amino acid described above, e.g., piperidine-2-carboxylic acid, naphthylalanine, tryptophan, or phenylalanine. In some embodiments, the chirality of $AA_{H1}$, $AA_{H2}$, and $AA_{H3}$ can be selected to improve cytosolic uptake efficiency, e.g., as described above, where $AA_{H1}$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SAS of less than or equal to $AA_{H1}$ and/or $AA_{H2}$.

In some embodiments, $AA_{H1}$ and $AA_{H2}$ have the same or opposite chirality. In certain embodiments, $AA_{H1}$ and $AA_{H2}$ have the opposite chirality. Accordingly, in some embodiments, the CPPs disclosed herein include at least one of the following sequences: D-$AA_{H2}$-L-$AA_{H1}$-R-r; L-$AA_{H2}$-D-$AA_{H1}$-r-R; R-r-D-$AA_{H1}$-L-$AA_{H2}$; or r-R-L-$AA_{H1}$-D-$AA_{H1}$, wherein each of D-$AA_{H1}$ and D-$AA_{H2}$ is a hydrophobic amino acid having a D configuration, and each of L-$AA_{H1}$ and L-$AA_{H2}$ is a hydrophobic amino acid having an L configuration. In some embodiments, each of D-$AA_{H1}$ and D-$AA_{H2}$ is independently selected from the group consisting of D-pip, D-nal, D-trp, and D-phe. In particular embodiments, D-$AA_{H1}$ or D-$AA_{H2}$ is D-nal. In other particular embodiments, D-$AA_{H1}$ is D-nal. In some embodiments, each of L-$AA_{H1}$ and L-$AA_{H2}$ is independently selected from the group consisting of L-Pip, L-Nal, L-Trp, and L-Phe. In particular embodiments, each of L-AA$_{H1}$ and L-AA$_{H2}$ is L-Nal. In other particular embodiments, L-AA$_{H1}$ is L-Nal.

As discussed above, the disclosure provides for various modifications to a cyclic peptide sequence which may improve cytosolic delivery efficiency. In some embodiments, improved cytosolic uptake efficiency can be measured by comparing the cytosolic delivery efficiency of the CPP having the modified sequence to a proper control sequence. In some embodiments, the control sequence does not include a particular modification (e.g., matching chirality of R and AA$_{H1}$) but is otherwise identical to the modified sequence. In other embodiments, the control has the following sequence: cyclic(FΦRRRRQ) (SEQ ID NO: 65).

As used herein cytosolic delivery efficiency refers to the ability of a CPP to traverse a cell membrane and enter the cytosol. In embodiments, cytosolic delivery efficiency of the CPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a CPP (or a CPP-cargo conjugate) over the concentration of the CPP (or the CPP-cargo conjugate) in the growth medium. Relative cytosolic delivery efficiency refers to the concentration of a CPP in the cytosol compared to the concentration of a control CPP in the cytosol. Quantification can be achieved by fluorescently labeling the CPP (e.g., with a FTIC dye) and measuring the fluorescence intensity using techniques well-known in the art.

In particular embodiments, relative cytosolic delivery efficiency is determined by comparing (i) the amount of a CPP of the invention internalized by a cell type (e.g., HeLa cells) to (ii) the amount of the control CPP internalized by the same cell type. To measure relative cytosolic delivery efficiency, the cell type may be incubated in the presence of a cell-penetrating peptide of the invention for a specified period of time (e.g., 30 minutes, 1 hour, 2 hours, etc.) after which the amount of the CPP internalized by the cell is quantified using methods known in the art, e.g., fluorescence microscopy. Separately, the same concentration of the control CPP is incubated in the presence of the cell type over the same period of time, and the amount of the control CPP internalized by the cell is quantified.

In other embodiments, relative cytosolic delivery efficiency can be determined by measuring the IC$_{50}$ of a CPP having a modified sequence for an intracellular target, and comparing the IC$_{50}$ of the CPP having the modified sequence to a proper control sequence (as described herein).

Non-limiting examples of suitable cyclic cell penetrating peptide are provided in Table 4. The CPP sequence in the polypeptides of the present disclosure can include any of the CPP sequences provided in Table 4, or a subset of amino acids in the CPPs provided in Table 4.

TABLE 4

| ID | CPP Sequence |
|---|---|
| PCT 1 | FΦRRR (SEQ ID NO: 66) |
| PCT 2 | FΦRRRC (SEQ ID NO: 67) |
| PCT 3 | FΦRRRU (SEQ ID NO: 68) |
| PCT 4 | RRRΦF (SEQ ID NO: 69) |
| PCT 5 | RRRRΦF (SEQ ID NO: 70) |
| PCT 6 | FΦRRRR (SEQ ID NO: 71) |
| PCT 7 | FφrRrR (SEQ ID NO: 72) |
| PCT 8 | FφrRrR (SEQ ID NO: 72) |
| PCT 9 | FΦRRRR (SEQ ID NO: 71) |
| PCT 10 | fΦRrRr (SEQ ID NO: 73) |
| PCT 11 | RRFRΦR (SEQ ID NO: 74) |
| PCT 12 | FRRRRΦ (SEQ ID NO: 75) |
| PCT 13 | rRFRΦR (SEQ ID NO: 76) |
| PCT 14 | RRΦFRR (SEQ ID NO: 77) |
| PCT 15 | CRRRRFW (SEQ ID NO: 11) |
| PCT 16 | FfΦRrRr (SEQ ID NO: 78) |
| PCT 17 | FFΦRRRR (SEQ ID NO: 79) |
| PCT 18 | RFRFRΦR (SEQ ID NO: 80) |
| PCT 19 | URRRRFW (SEQ ID NO: 12) |
| PCT 20 | CRRRRFW (SEQ ID NO: 13) |
| PCT 21 | FΦRRRRQK (SEQ ID NO: 81) |
| PCT 22 | FΦRRRRQC (SEQ ID NO: 82) |
| PCT 23 | fΦRrRrR (SEQ ID NO: 83) |
| PCT 24 | FΦRRRRR (SEQ ID NO: 84) |
| PCT 25 | RRRRΦFDΩC (SEQ ID NO: 85) |
| PCT 26 | FΦRRR (SEQ ID NO: 66) |
| PCT 27 | FWRRR (SEQ ID NO: 14) |
| PCT 28 | RRRΦF (SEQ ID NO: 69) |
| PCT 29 | RRRWF (SEQ ID NO: 15) |
| SAR 1 | FΦRRRR (SEQ ID NO: 71) |
| SAR 19 | FFRRR (SEQ ID NO: 16) |
| SAR 20 | FFrRr (SEQ ID NO: 86) |
| SAR 21 | FFRrR (SEQ ID NO: 87) |
| SAR 22 | FRFRR (SEQ ID NO: 17) |
| SAR 23 | FRRFR (SEQ ID NO: 18) |
| SAR 24 | FRRRF (SEQ ID NO: 19) |
| SAR 25 | GΦRRR (SEQ ID NO: 88) |
| SAR 26 | FFFRA (SEQ ID NO: 20) |
| SAR 27 | FFFRR (SEQ ID NO: 21) |
| SAR 28 | FFRRRR (SEQ ID NO: 22) |
| SAR 29 | FRRFRR (SEQ ID NO: 23) |
| SAR 30 | FRRRFR (SEQ ID NO: 24) |
| SAR 31 | RFFRRR (SEQ ID NO: 25) |
| SAR 32 | RFRRFR (SEQ ID NO: 26) |

TABLE 4-continued

| ID | CPP Sequence |
|---|---|
| SAR 33 | FRFRRR (SEQ ID NO: 27) |
| SAR 34 | FFFRRR (SEQ ID NO: 28) |
| SAR 35 | FFRRRF (SEQ ID NO: 29) |
| SAR 36 | FRFFRR (SEQ ID NO: 30) |
| SAR 37 | RRFFFR (SEQ ID NO: 31) |
| SAR 38 | FFRFRR (SEQ ID NO: 32) |
| SAR 39 | FFRRFR (SEQ ID NO: 33) |
| SAR 40 | FRRFFR (SEQ ID NO: 34) |
| SAR 41 | FRRFRF (SEQ ID NO: 35) |
| SAR 42 | FRFRFR (SEQ ID NO: 36) |
| SAR 43 | RFFRFR (SEQ ID NO: 37) |
| SAR 44 | GΦRRRR (SEQ ID NO: 89) |
| SAR 45 | FFFRRRR (SEQ ID NO: 38) |
| SAR 46 | RFFRRRR (SEQ ID NO: 39) |
| SAR 47 | RRFFRRR (SEQ ID NO: 40) |
| SAR 48 | RFFFRRR (SEQ ID NO: 41) |
| SAR 49 | RRFFFRR (SEQ ID NO: 42) |
| SAR 50 | FFRRFRR (SEQ ID NO: 43) |
| SAR 51 | FFRRRRF (SEQ ID NO: 44) |
| SAR 52 | FRRFFRR (SEQ ID NO: 45) |
| SAR 53 | FFFRRRRR (SEQ ID NO: 46) |
| SAR 54 | FFFRRRRRR (SEQ ID NO: 47) |
| SAR 55 | FΦRrRr (SEQ ID NO: 90) |
| SAR 56 | XXRRRR (SEQ ID NO: 48) |
| SAR 57 | FfFRrR (SEQ ID NO: 91) |
| SAR 58 | fFfrRr (SEQ ID NO: 92) |
| SAR 59 | fFfRrR (SEQ ID NO: 93) |
| SAR 60 | FfFrRr (SEQ ID NO: 94) |
| SAR 61 | fFφrRr (SEQ ID NO: 95) |
| SAR 62 | fΦfrRr (SEQ ID NO: 96) |
| SAR 63 | φFfrRr (SEQ ID NO: 97) |
| SAR 64 | FΦrRr (SEQ ID NO: 98) |
| SAR 65 | fΦrRr (SEQ ID NO: 99) |
| SAR 66 | Ac-(Lys-fFRrRrD) (SEQ ID NO: 100) |
| SAR 67 | Ac-(Dap-fFRrRrD) (SEQ ID NO: 101) |
| SAR 68 | CWWRRRRC (SEQ ID NO: 102) 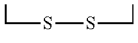 |
| SAR 69 | CWWVRRRRC (SEQ ID NO: 103) 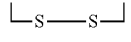 |
| SAR 70 | CFWRRRRC (SEQ ID NO: 104) 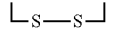 |
| SAR 71 | CWWWRRRC (SEQ ID NO: 105) 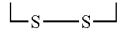 |
| Pin1 15 | Pip-Nal-Arg-Glu-arg-arg-glu (SEQ ID NO: 106) |
| Pin1 16 | Pip-Nal-Arg-Arg-arg-arg-glu (SEQ ID NO: 107) |
| Pin1 17 | Pip-Nal-Nal-Arg-arg-arg-glu (SEQ ID NO: 108) |
| Pin1 18 | Pip-Nal-Nal-Arg-arg-arg-Glu (SEQ ID NO: 109) |
| Pin1 19 | Pip-Nal-Phe-Arg-arg-arg-glu (SEQ ID NO: 110) |
| Pin1 20 | Pip-Nal-Phe-Arg-arg-arg-Glu (SEQ ID NO: 111) |
| Pin1 21 | Pip-Nal-phe-Arg-arg-arg-glu) (SEQ ID NO: 112) |
| Pin1 22 | Pip-Nal-phe-Arg-arg-arg-Glu (SEQ ID NO: 113) |
| Pin1 23 | Pip-Nal-nal-Arg-arg-arg-Glu (SEQ ID NO: 114) |
| Pin1 24 | Pip-Nal-nal-Arg-arg-arg-glu (SEQ ID NO: 115) |
| Rev-13 | [Pim-RQRR-Nlys]GRRR[b] (SEQ ID NO: 116) |
| hLF | KCFQWQRNMRKVRGPPVSC (SEQ ID NO: 117)  |
| cTat | [KrRrGrKkRrE][c] (SEQ ID NO: 118) |
| cR10 | [KrRrRrRrRrRE][c] (SEQ ID NO: 119) |
| L-50 | [RVRTRGKRRIRRpP] (SEQ ID NO: 120) |
| L-51 | [RTRTRGKRRIRVpP] (SEQ ID NO: 121) |
| [WR]4 | [WRWRWRWR] (SEQ ID NO: 49) |
| MCoTI-II | [GGVCPKILKKCRRDSDCPGACICRGNGYCGSGSD] (SEQ ID NO: 122) 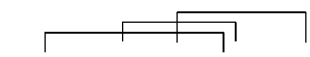 |

TABLE 4-continued

| ID | CPP Sequence |
|---|---|
| Rotstein et al. Chem. Eur. J. 2011 | [P-Cha-r-Cha-r-Cha-r-Cha-r-G]$^d$ (SEQ ID NO: 123) |
| Lian et al. J. Am. Chem. Soc. 2014 | Tm(SvP-F$_2$Pmp-H)-Dap-(FΦRRRR-Dap)]$^f$ (SEQ ID NO: 124) |
| Lian et al. J Am. Chem. Soc. 2014 | [Tm(a-Sar-D-pThr-Pip-ΦRAa)-Dap-(FΦRRRR-Dap)]$^f$ (SEQ ID NO: 125) |
| IA8b | [CRRSRRGCGRRSRRCG]$^g$ (SEQ ID NO: 127) |
| Dod-[R$_5$] | [K(Dod)RRRR] (SEQ ID NO: 128) |
| LK-3 | LKKLCKLLKKLCKLAG (SEQ ID NO: 129) <br>     |      | <br> LKKLCKLLKKLCKLAG (SEQ ID NO: 129) |
|  | RRRR-[KRRRE]$^c$ (SEQ ID NO: 130) <br> RRR-[KRRRRE]$^c$ (SEQ ID NO: 131) <br> RR-[KRRRRRE]$^c$ (SEQ ID NO: 132) <br> R-[KRRRRRRE]$^c$ (SEQ ID NO: 133) |
| [CR]$_4$ | [CRCRCRCR] (SEQ ID NO: 134) |
| cyc3 | [Pra-LRKRLRKFRN-AzK]$^h$ (SEQ ID NO: 135) |
| PMB | T-Dap-[Dap-Dap-f-L-Dap-Dap-T] (SEQ ID NO: 136) |
| GPMB | T-Agp-[Dap-Agp-f-L-Agp-Agp-T] (SEQ ID NO: 137) |
| CPP1 | FΦRRRR (SEQ ID NO: 71) |
| CPP12 | FfΦRrRr (SEQ ID NO: 78) |
| CPP9 | fΦRrRr (SEQ ID NO: 73) |
| CPP11 | fΦRrRrR (SEQ ID NO: 83) |
| CPP18 | FϕrRrR (SEQ ID NO: 72) |
| CPP13 | FϕrRrR (SEQ ID NO: 72) |
| CPP6 | FΦRRRRR (SEQ ID NO: 84) |
| CPP3 | RRFRΦR (SEQ ID NO: 74) |
| CPP7 | FFΦRRRR (SEQ ID NO: 79) |
| CPP8 | RFRFRΦR (SEQ ID NO: 80) |
| CPP5 | FΦRRR (SEQ ID NO: 66) |
| CPP4 | FRRRRΦ (SEQ ID NO: 75) |
| CPP10 | rRFRΦR (SEQ ID NO: 76) |
| CPP2 | RRΦFRR (SEQ ID NO: 77) |

Φ, L-2-naphthylalanine;
Pim, pimelic acid;
Nlys, lysine peptoid residue;
D-pThr, D-phosphothreonine;
Pip, L-piperidine-2-carboxylic acid;
Cha, L-3-cyclohexyl-alanine;
Tm, trimesic acid;
Dap, L-2,3-diaminopropionic acid;
Sar, sarcosine;
F$_2$Pmp, L-difluorophosphonomethyl phenylalanine;
Dod, dodecanoyl;
Pra, L-propargylglycine;
AzK, L-6-Azido-2-amino-hexanoic;
Agp, L-2-amino-3-guanidinylpropionic acid;
$^b$Cyclization between Pim and Nlys;
$^c$Cyclization between Lys and Glu;
$^d$Macrocyclization by multicomponent reaction with aziridine aldehyde and isocyanide;
$^e$Cyclization between the main-chain of Gln residue;
$^f$N-terminal amine and side chains of two Dap residues bicyclized with Tm;
$^g$Three Cys side chains bicyclized with tris(bromomethyl)benzene;
$^h$Cyclization by the click reaction between Pra and Azk.

The cell-penetrating peptide sequences of the present disclose can include any of those disclosed in US 2017/0355730 A1, WO/2018/098231 (and the US patent application publication related thereto), and U.S. Provisional application No. 62/669,146 (and the US patent application publication related thereto), each of which are herein incorporated by reference in its entirety for all purposes.

In certain embodiments, the cytosolic delivery efficiency of a particular CPP used in the bicyclic polypeptide of the claimed invention, may also be dependent on the sequence of Xm. In further embodiments of the invention, a particular CPP/Xm bicyclic polypeptide may have an improved cytosolic delivery efficiency of about 1.1 fold to about 30 fold, compared to an bicyclic polypeptide having an identical CPP and a different Xm, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold inclusive of all values and subranges therebetween. In further embodiments of the invention, a particular CPP/Xm bicyclic polypeptide may have an improved cytosolic delivery efficiency of about 1.1 fold to about 30 fold, compared to an bicyclic polypeptide having an identical Xm and a different CPP, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold inclusive of all values and subranges therebetween.

In certain embodiments, L-2,3-diaminopropionic acid may be conjugated to the C-terminal of the CPP sequences in Table 4 to facilitate conjugation to the L. In other embodiments, the C-terminal amino acid of the CPP sequences in listed in Table 4 may be substituted with L-2,3-diaminopropionic acid to facilitate conjugation to the L.

Additionally, the CPP used in the polypeptide conjugates and methods described herein can include any sequence disclosed in: U.S. application Ser. No. 15/312,878; U.S. application Ser. No. 15/360,719; U.S. App. No. 62/438,141, and U.S. App. No. 62/507,483, each of which is incorporated by reference in its entirety for all purposes.

Linker

In various embodiments, the polypeptides disclosed herein comprise a linker ("L"). The L may be any appropriate moiety which is capable of forming a covalent bond to the Xm, CPP, or a combination thereof, to form the bicyclic peptides of the present disclosure. In certain embodiments, the L is a pharmaceutically acceptable moiety. In some embodiments, the L is any appropriate trivalent radical.

In some embodiments, the L is may be an alkylene, alkenylene, alkynylene, aryl, cycloalkyl, cycloalkenyl, cycloalkynyl, heterocyclyl, heteroaryl, or N-alkyl, each of which can be optionally substituted as defined herein.

"Alkylene" or "alkylene chain" refers to a fully saturated, straight or branched trivalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. Unless stated otherwise specifically in the specification, an alkylene chain can be optionally substituted as described herein.

"Alkenylene" or "alkenylene chain" refers to a straight or branched trivalent hydrocarbon chain radical, having from two to forty carbon atoms, and having one or more carbon-carbon double bonds. Non-limiting examples of $C_2$-$C_{40}$ alkenylene include ethene, propene, butene, and the like. Unless stated otherwise specifically in the specification, an alkenylene chain can be optionally substituted.

"Alkynylene" or "alkynylene chain" refers to a straight or branched trivalent hydrocarbon chain radical, having from two to forty carbon atoms, and having one or more carbon-carbon triple bonds. Non-limiting examples of $C_2$-$C_{40}$ alkynylene include ethynylene, propargylene and the like. Unless stated otherwise specifically in the specification, an alkynylene chain can be optionally substituted.

"Aryl" refers to a hydrocarbon ring system trivalent radical comprising hydrogen, 6 to 40 carbon atoms and at least one aromatic ring. For purposes of this invention, the aryl trivalent radical can be a monocyclic, bicyclic, tricyclic or tetracyclic ring system, which can include fused or bridged ring systems. Aryl trivalent radicals include, but are not limited to, aryl trivalent radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group can be optionally substituted.

"Cycloalkyl" refers to a stable non-aromatic monocyclic or polycyclic fully saturated hydrocarbon trivalent radical having from 3 to 40 carbon atoms and at least one ring, wherein the ring consists solely of carbon and hydrogen atoms, which can include fused or bridged ring systems. Monocyclic cycloalkyl trivalent radicals include, for example, cyclopropyl, cyclobutyl, cyclopentyl, cyclohexyl, cycloheptyl, and cyclooctyl. Polycyclic cycloalkyl trivalent radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon trivalent radical having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon trivalent radical having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyl radicals include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable 3- to 20-membered non-aromatic ring trivalent radical which consists of two to twelve carbon atoms and from one to six heteroatoms selected from the group consisting of nitrogen, oxygen and sulfur. Heterocyclcl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-alkyl" refers to a alkyl radical as defined above containing at least one nitrogen and where a point of attachment of the alkyl radical to the rest of the molecule is through a nitrogen atom in the N-alkyl radical. Unless stated otherwise specifically in the specification, a N-alkyl group can be optionally substituted.

The term "substituted" used herein means any of the above groups (i.e., alkylene, alkenylene, alkynylene, aryl, carbocyclyl, cycloalkyl, cycloalkenyl, cycloalkynyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more hydrogen atoms on any of the above groups are replaced by a substituent listed in this paragraph, and the substituent forms a covalent bond with the CPP or the Xm. For example, in certain embodiments, any of the above groups (i.e., alkylene, alkenylene, alkynylene, aryl, carbocyclyl, cycloalkyl, cycloalkenyl, cycloalkynyl, heterocyclyl, and/or heteroaryl) can be substituted at one or more positions with a carboxylic acid (i.e., $-C(=O)OH$) which forms an amide bond with an amino group in the CPP and/or Xm (e.g., the N-terminus of the CPP or the Xm, or an amino group on a side chain of an amino acid in the CPP and/or Xm).

In some embodiments, the L is an aryl ring, which is independently substituted at three separate locations on the aryl ring. In certain embodiments, the aryl ring is a phenyl ring.

In some embodiments, the L forms a covalent bond with an amino acid in the Xm and/or the CPP. The resulting moiety, when L forms a bond to Xm and/or the CPP, to form the bicyclic polypeptides described herein, are referred to as R1, R2, and R3. In other embodiments, the L forms a covalent bond with the N- or C-terminus of an amino acid in the Xm and/or the CPP, or the side chain of an amino acid in the Xm and/or the CPP.

In some embodiments, each of R1, R2, and R3 are independently selected form an amide, an ester, and triazole, and combinations thereof. In further embodiments, each of R1, R2, and R3 are and an amide.

In certain embodiments, the bicyclic polypeptide has the structure of Formula 1A, 1B, 1C. or 1D, wherein each $AA_L$, when present, is, independently, selected from a D or L amino acid.

Each $AA_L$ may be a natural or non-natural amino acid as described above. In particular embodiments, p is one and $AA_L$ is Dap.

In some embodiments, the precursor to L (i.e., the moiety before L forms one or more covalent bonds to the Xm and/or CPP) is $L-(C(O)OH)_3$. In some such embodiments, the precursor to L has a structure according to Formula 4:

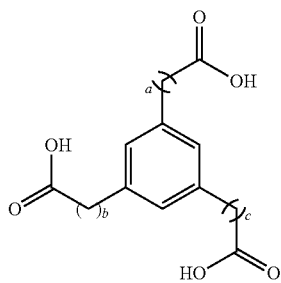

(4)

wherein a, b, and c are independently selected from a number from 0 to 10.

In various embodiments, the disclosure provides for bicyclic polypeptides according to Formula 5A or 5B:

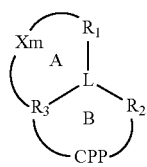

(5A)

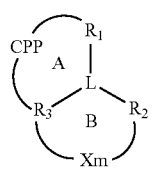

(5B)

wherein:
the CPP comprises a sequence according to Formula 2:

$(AAu)m-AA_1-AA_2-AA_3-AA_4-(AAz)n$  2 wherein:
  each of $AA_1$, $AA_2$, $AA_3$, and $AA_4$, are independently selected from a D or L amino acid,
  each of $AA_u$, and $AA_z$, at each instance and when present, are independently selected from a D or L amino acid, and
  m and n are independently selected from a number from 0 to 6; and
wherein:
  at least two of $AA_u$, when present, $AA_1$, $AA_2$, $AA_3$, $AA_4$, and $AA_z$, when present, are independently arginine, and
  at least two of $AA_u$, when present, $AA_1$, $AA_2$, $AA_3$, $AA_4$, and $AA_z$, when present, are independently a hydrophobic amino acid;
Xm is a peptide sequence is a 3-10 amino acid sequence comprising one or more amino acids selected from G, g, W, w, I, i, Y, y, A, and a (SEQ ID NO: 64);
L is a linker moiety; and
each of $R_1$, $R_2$, and $R_3$ are independently, a bonding moiety,
  wherein the bonding moiety is formed when Xm, CPP, or a combination thereof, covalently bind to L to form the bicyclic polypeptide.

In various embodiments, the disclosure provides for bicyclic polypeptides according to Formula 5C or 5D:

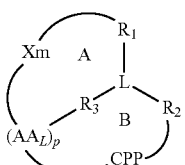

(5C)

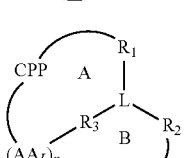

(5D)

wherein:
the CPP comprises a sequence according to Formula 2:

$(AAu)m-AA_1-AA_2-AA_3-AA_4-(AAz)n$  2 wherein:
  each of $AA_1$, $AA_2$, $AA_3$, and $AA_4$, are independently selected from a D or L amino acid,
  each of $AA_u$, and $AA_z$, at each instance and when present, are independently selected from a D or L amino acid, and m and n are independently selected from a number from 0 to 6; and
wherein:
  at least two of $AA_u$, when present, $AA_1$, $AA_2$, $AA_3$, $AA_4$, and $AA_z$, when present, are independently arginine, and
  at least two of $AA_u$, when present, $AA_1$, $AA_2$, $AA_3$, $AA_4$, and $AA_z$, when present, are independently a hydrophobic amino acid;
Xm is a peptide sequence is a 3-10 amino acid sequence comprising one or more amino acids selected from G, g, W, w, I, i, Y, y, A, and a (SEQ ID NO: 64);
$AA_L$ at each instance is an amino acid;
p is selected from a number from 0 to 3 (e.g., 0, 1, 2, or 3);
L is a linker moiety; and
each of $R_1$, $R_2$, and $R_3$ are independently, a bonding moiety,
  wherein the bonding moiety is formed when Xm, CPP, or a combination thereof, covalently bind to L to form the bicyclic polypeptide.

In further embodiments of the invention, the CPP of the bicyclic polypeptide of Formula 5A-5D comprises a sequence according to Formula 3A-D:

$(AA_u)_m — AA_{H2} — AA_{H1} — R — r — (AA_z)_n,$  3-A $(AA_u)_m — r — R — AA_{H1} — AA_{H2} — (AA_z)_n$  3-B $(AA_u)_m — AA_{H2} — AA_{H1} — r — R — (AA_z)_n,$ and  3-C $(AA_u)_m — R — r — AA_{H1} — AA_{H2} — (AA_z)_n$  3-D wherein:
each of $AA_{H1}$ and $AA_{H2}$ are independently a hydrophobic amino acid;
at each instance and when present, each of $AA_U$ and $AA_Z$ are independently any amino acid; and m and n are independently selected from a number from 0 to 6.

In still further embodiments of the invention the Xm peptide sequence of the bicyclic polypeptide of Formulae 1A-1D and 5A-5D is a 3-7 amino acid sequence comprising a sequence selected from WI, IW, Wi, iW, wI, Iw, iw, wi.

In yet further embodiments of the invention, the Xm peptide sequence of the bicyclic polypeptide of Formulae 1A-1D and 5A-5D is a 4-7 amino acid sequence comprising a sequence selected from the group consisting of: GWIY (SEQ ID NO:1); GWIYA (SEQ ID NO:2); GWIYa (SEQ ID NO: 50); AGWIY (SEQ ID NO:3); aGWIY (SEQ ID NO: 51); AWIYA (SEQ ID NO:4); GAIYA (SEQ ID NO:5); GWAYA (SEQ ID NO:6); GWIAA (SEQ ID NO:7); GWIYA (SEQ ID NO:8); GAIAA (SEQ ID NO:9); and GAAAA (SEQ ID NO:10), and the inverse of such sequences (SEQ ID NOs: 52-63).

Methods of Treatment

In some embodiments, the polypeptides disclosed herein inhibit the NEMO-IKKα/β interaction by at least about 10%, e.g., about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, and about 100%, inclusive of all values and subranges therebetween.

As used herein, the terms "inhibit," inhibited," "inhibition," "inhibiting" or other derivations or variations thereof refer to the activity of a particular enzyme which is reduced by using an inhibitor. In some embodiments, "inhibition" can refer to complete loss of function of an enzyme or a reduction of the activity of the enzyme (e.g., by about 1% or more). The level of reduction is compared to a comparable host cell of the same species which is not treated by the inhibitor.

In some embodiments, the polypeptides disclosed herein have an $IC_{50}$ of about 10 μM or less when measured for the NEMO-IKKα/β interaction, e.g., about 9 about 8 about 7 about 6 about 5 about 4 about 3 about 2 about 1 about 0.9 about 0.8 about 0.7 about 0.6 about 0.5 about 0.4 about 0.3 about 0.2 about 0.1 μM, about 0.09 about 0.08 about 0.07 about 0.06 about 0.05 about 0.04 about 0.03 about 0.02 or about 0.01 μM or less, inclusive of all values and subranges therebetween. In particular embodiments, polypeptides have an IC50 of about 1.0 μM or less when measured for the NEMO-IKKα/β interaction.

Methods of Making

The polypeptide conjugates described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high-performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl;

for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-dii sopropylcarbo-diimide (DIC) or O-benzotri azol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazo-lidinyl)phosphine chloride (BOPC1), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N, N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octa-decylsilyl-silica bonded phase column packing.

Methods of Administration

In vivo application of the disclosed polypeptide conjugates, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, intranasal, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

Example 1. Design and Synthesis of Combinatorial Library of Cell-Permeable Bicyclic Peptides A bicyclic peptide library featuring random peptide sequences of 3-6 residues in the first ring (A ring) and 12 different CPP sequences in the second ring (B ring) was designed and prepared (FIG. 1). The peptide library was synthesized on 2 g of TentaGel S NH2 resin (130 µm) by modifying a previously reported protocol disclosed in Lian et al. (Am. Chem. Soc. 2013, 135, 11990-11995), which is incorporated by reference herein in its entirety. Library screening was also performed according to previously established protocols in Lian et al. (Am. Chem. Soc. 2013, 135, 11990-11995). In brief, approximately 600 mg of the bicyclic peptide library was swollen in DCM and washed extensively with DMF, ddH$_2$O and finally incubated overnight at 4° C. in 1.0 mL of blocking buffer (30 mM sodium phosphate, pH 7.4, 150 mM NaCl, 0.05% Tween 20, 3% BSA and 0.1% gelatin). The solution was drained and the resin was resuspended in blocking buffer containing 1.0 µM biotinylated GST-NEMO for 4 hours at 4° C. Unbound NEMO was washed away with blocking buffer and the beads were resuspended in 10 mL of blocking buffer. Twenty µL of M280 streptavidin-coated Dynabeads (Invitrogen) was added to the solution and allowed to incubate on a rotary wheel for 1 hour at 4° C. The magnetic beads were isolated from the bulk by using a TA Dynal MPC-1 magnetic particle concentrator (Invitrogen). Hit beads were transferred to a Bio-Spin column (0.8 mL, BioRad) and incubated in blocking buffer containing 1.0 µM biotinylated GST-NEMO for 4 hours at 4° C. The solution was drained and the resin was washed with blocking buffer to remove unbound protein. The resin was resuspended in 1 mL of blocking buffer and streptavidin-alkaline phosphatase (SA-AP) conjugate was added to the tube (1 mg/mL final concentration). After 10 minutes at 4° C. the solution was drained and the beads were quickly washed with 1 mL of blocking buffer (3×) and 1 mL of staining buffer (30 mM Tris pH 8.5, 100 mM NaCl, 5 mM MgCl$_2$, and 20 µM ZnCl$_2$) (3×). The resin was resuspended in 1.5 mL of staining buffer in a petri dish and 150 µL of a 5-bromo-4-chloro-3-indolyl-phosphate (BCIP) solution (5 mg/mL) was added. After 30 minutes, 50 µL of 1 M HCl was added to quench the reaction and the intensely turquoise positive beads were isolated under a dissecting microscope. The sequences of hit beads were determined using partial Edman degradation-mass spectrometry (PED-MS) as previously described in Thakkar et al. (Anal. Chem. 2006, 78, 5935-5939), which is incorporated by reference herein in its entirety.

The resulting peptide sequences in the A ring were constructed through combinatorial synthesis using a set of 24 proteinogenic and unnatural amino acids (e.g., D-amino acids). The 12 CPP sequences consisted of different combinations of two or three aromatic hydrophobic residues (L- or D-Phe and L- or D-naphthylalanine) and three or four L- or D-arginine residues and were prepared by parallel synthesis. Because the NEMO surface near the IKK-binding site is negatively charged (vide infra), in addition to ensuring cell penetration, some of the positively charged CPP sequences might also interact electrostatically with the negatively charged NEMO surface. The bicyclic library has a theoretical diversity of 2.4×10$^9$ and was synthesized on 130-µm TentaGel beads in the one bead-two compound (OBTC) format, with each bead displaying a unique bicyclic peptide on its surface layer and a linear peptide of identical sequence in its inner layer as an encoding tag. The library design also included a propargylglycine-β-alanine-hydroxylmethylbenzoyl ester (Pra-B-Hmb) linker, which was intended for selective on-bead fluorescent labeling and release of the bicyclic peptide for an additional round of in-solution screening, although the latter turned out to be unnecessary.

Approximately 600 mg of the library (about 600,000 different compounds) was screened for binding to NEMO in two different rounds as detailed under Methods, resulting in 12 unique hit sequences. Ten of these 12 peptides were resynthesized and tested for inhibition of the NEMO-IKKβ interaction by using a homogenous time-resolved fluorescence (HTRF) assay. All 10 peptides inhibited the NEMO-IKKβ interaction with IC50 values of 3.4-28 µM. The three most potent compounds were labelled with fluorescein and their cellular uptake into HeLa cells was quantitated by flow cytometry analysis. All three peptides were cell-permeable and had similar cell entry efficiency. Peptide 2 (Table 5) was selected for further optimization, because it showed the highest potency in the HTRF assay, with an IC50 value of 3.4 µM (FIG. 2A).

For flow cytometry analysis, HeLa cells were seeded into 12-well plates (1.5×10$^5$ cells per well) 24 hours before treatment. The next day, 5 µM FITC-labeled peptide in DMEM containing 10% FBS was added to each well and allowed to incubate at 37° C. for 2 hours. After compound treatment, the cells were washed with DPBS, detached from the plate with trypsin (0.25%), diluted in DMEM containing 10% FBS and pelleted at 250 g for 5 min. This washing process was repeated once to remove any free compound and left over trypsin. The washed pellet was resuspended in DPBS with 1% FBS and analyzed on a BD LSR II flow cytometer. Data presented were the mean±SD of three independent experiments.

Recombinant GST-NEMO (20 nM), biotin-IKKβKK/RR (701-745) (50 nM), streptavidin labeled with d2 acceptor (2.5 µg/mL), anti-GST monoclonal antibody labeled with Tb donor (2.5 µg/mL), and varying concentrations of peptide (0-100 µM) were mixed in PBS containing 1 mM TCEP and 0.01% Triton X-100 (total volume 20 µL) in a 384-well plate. The plate was incubated for 2 hOURS at room temperature to establish an equilibrium. The HTRF signals were measured on a Tecan Infinite M1000 Pro microplate reader and plotted as a function of the peptide concentration. The data was analyzed using GraphPad Prism 6.0 and IC50 values were obtained by fitting the data to the dose-response inhibition curves. Data presented were the mean±SD of three independent experiments.

In general, for protein expression and purification, *Escherichia coli* BL21(DE3) cells were transformed with a pGEX4T3-NEMO(1-196) plasmid and grown at 37° C. in Luria broth supplemented with 0.05 mg/mL ampicillin to an OD600 of 0.4. Expression of GST-NEMO was induced by the addition of isopropyl β-D-1-thiogalactopyranoside (150 µM final concentration). After five hours at 30° C., the cells were harvested by centrifugation. The cell pellet was suspended in 40 mL of lysis buffer (50 mM Tris-HCl, 100 mM NaCl, 0.5 mM MgCl2, 5 mM 3-mercaptoethanol, 0.1% Triton-X-100, pH 8.0), 100 µg/mL lysozyme, 100 µL of DNAse I (New England BioLabs), and 100 µL of Halt Protease Inhibitor Cocktail (EDTA-free) (Thermo Scientific). This mixture was stirred at 4° C. for 30 min and briefly sonicated (2×10 s pulses). The crude lysate was centrifuged to yield a clear supernatant, which was directly loaded onto a glutathione-Sepharose 4B column (GE Healthcare). The bound protein was eluted from the column with 10 mM glutathione in 50 mM Tris-HCl (pH 8.0), concentrated to 0.5 mL with the use of Amicon Ultra-15 centrifugal filter units (MWCO 10 kDa), and dialyzed against PBS before flash freezing.

An engineered prokaryotic expression plasmid pJCC04a, which encodes a fusion protein containing an N-terminal six-histidine tag, thioredoxin, a TEV protease cleavage site, and the K703R/K704R mutant form of IKKβ C-terminal fragment (amino acids 701-745) [His-thx-IKKbKK/RR (701-745)]. His-thx-IKKbKK/RR(701-745) was similarly expressed in *E. coli* BL21 (DE3) cells and purified by affinity chromatography using a HisTrap FF column (GE Healthcare). The fusion protein was eluted with 50 mM Tris-HCl (pH 8.0), 300 mM NaCl, 250 mM imidazole, 2 mM β-mercaptoethanol and treated with TEV protease (150 units for 1 mg of fusion protein) for 16 hours at 4° C. to remove the thioredoxin (thx). The resulting protease digestion mixture was reloaded onto the HisTrap column. The flow-through fraction was collected and concentrated to about 2 mg/mL using Amicon Ultra-15 centrifugal filter units (MWCO 10 kDa). The IKKbKK/RR(701-745) peptide was biotinylated by treatment with a 10-fold molar excess of biotin-NHS at 4° C. overnight. The biotinylated IKKbKK/RR(701-745) was purified by reversed-phase HPLC equipped with a C18 column and stored frozen at −80° C.

In addition, a medicinal chemistry campaign was conducted to investigate the NEMO-binding affinity and/or cell-permeability of peptide 2. In brief, we first modified the CPP motif in the B ring to improve cellular uptake. Addition of a 4th arginine to the CPP motif, either inside (Table 5, peptide 3) or outside the B ring (peptides 4 and 5) slightly decreased the cellular entry efficiency. Replacement of the second arginine with D-arginine increased the uptake efficiency by 4.2-fold (peptide 6). Therefore, FΦRrR (where Φ is L-naphthylalanine and r is D-arginine (SEQ ID NO: 66)) was chosen as the CPP motif and modified the A ring to improve the NEMO-binding affinity. Insertion of an Ala immediately N-terminal to the internal Dap residue (with the intention of creating an additional site of diversification) increased the binding affinity by 5.9-fold (IC50=1.0 μM for peptide 7; FIGS. 1 and 2A-2E).

In a fluorescence anisotropy (FA) assay, fluorescently labeled peptide 7 bound directly to NEMO with a KD value of 220±80 nM, but only weakly to a panel of control proteins (KD>10 The proteolytic stability of peptide 7 was assessed by incubation in human serum at 37° C. and quantitation of the remaining peptide as a function of time by analytical HPLC. Peptide 7 showed minimal degradation (<1%) after 20 hours of incubation. Under the same conditions, Antp-NBD (Table 5, peptide 1) was rapidly degraded with a half-life of about 20 minutes. Given its excellent proteolytic stability and respectable potency and cell permeability (163% relative to CPP1, a previously reported and relatively efficient cyclic CPP; FIGS. 2A and 2b), we selected peptide 7 (FIG. 1) for further characterization.

To gain insight into how peptide 7 interacts with NEMO, in silico docking of peptide 7 to the NEMO protein was performed. The all-atom 3D structure of peptide 7 was prepared in Maestro from the 2D structure (Schrodinger, LLC ver. 11.1) and relaxed using Polak-Ribier conjugate gradient minimization to resolve steric and torsional strain introduced during conversion. To account for the complex conformational landscape of a bicyclic peptide, a conformational ensemble of structures was obtained for peptide 7 using molecular dynamics. In brief, peptide 7 was parameterized using the OPLS3 force-field and then solvated in an orthorhombic periodic box containing 1867 TIP3P water molecules. The system was neutralized with the addition of three Cl− ions and then simulated for 1 ns at 303 K and 1.01 MPa, controlled using the Nose-Hoover thermostat and Martyna-Tobias-Klein barostat, respectively, through the Desmond software package. Structures corresponding to every 10 ps of the simulation were extracted using the Trajectory tool in Maestro. To ensure that the ensemble contains a diverse selection of initial compound geometries, the molecular dynamics structures were passed through the Macrocycle Conformational Sampling tool in MacroModel using the OPLS3 force-field. Generalized Born/Solvent Area water electrostatics were applied, sampling across a temperature range from 300 K to 1000 K using a global low-mode search over 50 simulation cycles. Redundant conformers (defined as a heavy-atom RMSD of ≤0.75 Å) were rejected, yielding an ensemble of 105 structures spanning an energy range of 20 kcal/mol, which were carried forward for docking.

The receptor was prepared from the reported crystal structure of a NEMO dimer (PDBID: 3V3B), by removing co-crystallized solvent and reconstructing incomplete side-chains using Prime (Schrodinger LLC). The binding site was defined as a 20-Å cube centered on the geometric mean of receptor residues Leu-93, Phe-97 and Val-104. Rigid-receptor/flexible-ligand docking was performed using extra-precision mode in Glide. Ligand flexibility was accounted for by applying a scaling factor of 0.8 to ligand atom van der Waals radii and the generation of 100,000 poses per ligand sampled, for a theoretical total of 100,000,000 poses sampled for peptide 7 during the combined docking runs. Top scoring poses were subjected to a brief round of energy minimization using Embrace (Schrodinger LLC) to remove any steric clashes resulting from van der Waals' radii scaling during docking. The final poses were analyzed and electrostatic potential surfaces generated using UCSF Chimera.

The best-scoring binding pose of peptide 7 shown in FIGS. 3A-3C. Peptide 7 binds to the canonical IKK-binding site on NEMO, with the peptide A ring partially inserted into a hydrophobic groove normally occupied by the NBD of IKKβ. The side chain of Tyr-4 is deeply inserted into a large hydrophobic pocket and excluded from the sol-vent (FIG. 3B). Ile-3 interacted intimately with a shallow hydrophobic pocket on the NEMO surface, whereas Trp-2 made surface contacts primarily through the pyrrole ring while the benzene ring was mostly solvent exposed.

The B ring (CPP ring) of peptide 7 made important interactions with NEMO. The three arginine residues of the CPP motif interact electrostatically with the acidic patch next to the NBD binding groove (FIG. 3B). Phe-7, which is a part of the CPP motif, was completely buried and made hydrophobic interaction with NEMO. Nal-8 was almost completely solvent exposed, although the naphthalene ring may make hydrophobic interactions with the NEMO surface.

To assess the validity of the molecular modeling results, we performed an "alanine scan" of peptide 7 by replacing each residue with an alanine (or D-alanine) and determining the IC50 values of the resulting peptides against the NEMO-IKKβ interaction (Table 5, peptides 11-19). Consistent with the modeling results, replacement of Trp-2, Ile-3, or Tyr-4 in the A ring with alanine significantly decreased the potency of the inhibitor (by 2- to 3-fold for peptides 12-14).

Substitution of Ala for Phe-7 (peptide 15), Nal-8 (peptide 16), or D-Arg at position 10 (peptide 18) also significantly de-creased the NEMO-binding affinity. Thus, both molecular modeling and alanine-scan results indicate that the CPP motif in the B ring also interacts with the NEMO protein and contributes to the overall binding affinity and specificity of peptide 7.

Based on the SAR data, we generated two negative control peptides by replacing two (Trp-2 and Tyr-4) or three of the NEMO-binding residues in the A ring (Trp-2, Ile-3, and Tyr-4) with Ala. The resulting peptides (peptides 20 and 21) have similar cellular entry efficiencies to peptide 7, but 16- and >100-fold lower NEMO-binding affinity, respectively (FIGS. 2A and 2B and Table 5). In general, the bicyclic peptide library strategy developed in this work should be applicable to the discovery of cell-permeable bicyclic peptides against numerous intracellular targets.

TABLE 5

Sequences, NEMO-binding affinities, and cell-permeability of peptide.

| Peptide ID | SEQ ID NO: | Sequence | IC$_{50}$ (µM) | Permeability (%) |
|---|---|---|---|---|
| 1 | 138 | RQIKIWPQNRRMKWKKGGTALDWSWLQTE | >40 | 35 |
| 2 | 139 | Tm(GWIY)Δ(FΦRRRΔ)-BBK | 3.4 ± 0.6 | 76 |
| 3 | 140 | Tm(GWIY)Δ(FΦRRRRΔ)-BBK | 1.5 ± 0.2 | 55 |
| 4 | 141 | Tm(GWIY)Δ(FΦRRRΔ)-RBK | 1.8 ± 0.3 | 71 |
| 5 | 142 | Tm(GWIY)Δ(FΦRRRΔ)-rBK | 1.3 ± 0.4 | 71 |
| 6 | 143 | Tm(GWIY)Δ(FΦRrRΔ)-BBK | 5.9 ± 0.6 | 322 |
| 7 | 144 | Tm(GWIYA)Δ(FΦRrRΔ)-BBK | 1.0 ± 0.1 | 163 |
| 8 | 145 | Tm(GWIYa)Δ(FΦRrRΔ)-BBK | 2.9 ± 0.1 | |
| 9 | 146 | Tm(AGWIY)Δ(FΦRrRΔ)-BBK | 2.2 ± 0.1 | |
| 10 | 147 | Tm(aGWIY)Δ(FΦRrRΔ)-BBK | 2.3 ± 0.3 | |
| 11 | 148 | Tm(AWIYA)Δ(FΦRrRΔ)-BBK | 1.2 ± 0.2 | |
| 12 | 149 | Tm(GAIYA)Δ(FΦRrRΔ)-BBK | 3.0 ± 0.3 | |
| 13 | 150 | Tm(GWAYA)Δ(FΦRrRΔ)-BBK | 1.7 ± 0.1 | |
| 14 | 151 | Tm(GWIAA)Δ(FΦRrRΔ)-BBK | 2.8 ± 0.3 | |
| 15 | 152 | Tm(GWIYA)Δ(AΦRrRΔ)-BBK | 1.9 ± 0.2 | |
| 16 | 153 | Tm(GWIYA)Δ(FARrRΔ)-BBK | 2.8 ± 0.2 | |
| 17 | 154 | Tm(GWIYA)Δ(FΦArRΔ)-BBK | 1.1 ± 0.3 | |
| 18 | 155 | Tm(GWIYA)Δ(FΦRaRΔ)-BBK | 2.1 ± 0.2 | |
| 19 | 156 | Tm(GWIYA)Δ(FΦRrAΔ)-BBK | 1.2 ± 0.2 | |
| 20 | 157 | Tm(GAIAA)Δ(FΦRrRΔ)-BBK | 16 ± 2 | 176 |
| 21 | 158 | Tm(GAAAA)Δ(FΦRrRΔ)-BBK | >100 | 110 |

Tm, trimesic acid; Δ, L-2,3-diaminopropionic acid; Φ, L-2-naphthylalanine; B, L-β-alanine; r, D-arginine.
See FIG. S$_1$ for detailed structures.
Cell-permeability values are relative to that of CPP$_1$ (100%).

Example 2. Inhibition of NF-κB Signaling by Bicyclic Peptidyl Inhibitors

The ability of the bicyclic peptidyl inhibitors to inhibit NF-κB Signaling was analyzed. The ability of peptide 7 to enter the cell and block the intracellular NEMO-IKK interaction was assessed by using HEK293(Luc) cells, which harbor a luciferase gene under the transcriptional control of NF-κB. For the NF-κB Luciferase Assays, culture media was exchanged for DMEM containing 10% FBS and 1% penicillin/streptomycin the day before seeding to remove hygromycin B. HEK293(Luc) cells were seeded in 50 µL of assay medium (DMEM, 10% FBS, and 1% penicillin/streptomycin) in an opaque 96-well microplate (3000 cells per well) and incubated overnight. The peptide inhibitors were added to the cells the next day in 5 µL of assay medium and the plate was incubated at 37° C. for 2 h. After that, 5 µL of assay media containing recombinant TNFα (final concentration 5 ng/mL) was added to the wells. The plate was then returned to the incubator for 4 h at 37° C. Finally, 50 µL of ONE-Step luciferase assay reagent was added to each well and after 10 minutes the luminescence was measured on a Tecan Infinite M1000 Pro microplate reader. Data presented were the mean±SD of at least three independent experiments (n=6 for basal activities).

In the absence of any inhibitor, treatment of HEK 293 (Luc) cells with TNFα activated the IKK complex and nuclear translocation of NF-κB, resulting in a 15-fold increase in the luciferase activity (FIG. 2C). Prior incubation of the cells with peptide 7 dose-dependently inhibited the TNFα-induced NF-κB activation with an IC$_{50}$ value of 10 µM (FIGS. 2C and 2D). Antp-NBD (peptide 1) also inhibited NF-κB activation, but with an IC$_{50}$ of about 41 µM, in agreement with previous reports. The two negative control peptides (peptide 20 and peptide 21) decreased the luciferase activity only at high concentrations.

It is to be noted that at very high concentrations, cationic CPPs may cause nonspecific cytotoxicity to mammalian cells and reduce the expression of the luciferase gene.

Further, at high concentrations (>10 µM), CPPs can directly cross the plasma membrane through a yet poorly defined "direct translocation" mechanism, in addition to endocytic uptake, resulting in much greater cytosolic entry efficiency. Both factors may cause artificially low cellular $IC_{50}$ values in the luciferase assay for poorly active peptides (such as Antp-NBD, peptide 20 and peptide 21). As discussed earlier, NEMO is not involved in the non-canonical NF-κB signaling pathway. A specific inhibitor against NEMO should not block the basal NF-κB activity, which has important physiological functions.

To test whether peptide 7 also affects the basal NF-κB activity, the luciferase assay was repeated in the absence of TNFα stimulation. As shown in FIG. 2C, peptide 7 did not inhibit the basal NF-κB activity. Instead, it caused a small but statistically significant increase in the basal NF-κB activity (about 1.5-fold). Such a small stimulatory effect was previously reported for Antp-NBD and attributed to increased availability of IKKα/β for the non-canonical NF-κB signaling pathway when the canonical pathway is blocked. To ascertain that inhibition of NF-κB signaling by peptide 7 is caused by disruption of the NEMO-IKK interaction, we treated HT29 colon cancer cells with peptide 7 and TNFα and examined the levels of phosphorylated (and activated) IKKβ and IκBα, which acts immediately downstream of the NEMO-IKK complex, by western blot analysis.

As expected, peptide 7 (0-25 µM) dose-dependently inhibited TNFα-induced phosphorylation of IKKβ, while the total intracellular IKKβ level was unchanged (FIG. 2E). For immunoblot analysis, HT29 cells were grown in a 6-well plate to 80-90% confluency in standard DMEM (Life Technologies) supplemented with 10% FBS and 1% penicillin-streptomycin sulfate at 37° C. in 5% CO2. The cells were treated with 0, 2, 10, or 25 µM peptide 7 for 2 hours followed by stimulation with TNFα (5 ng/ml) for 10 minutes. The cells were rapidly washed with cold PBS and trypsinized to detach from the plate. Following centrifugation and resuspension in PBS to remove any remaining trypsin the pelleted cells were lysed in 100 µl of Pierce™ RIPA Buffer (Thermo) containing protease and phosphatase inhibitors for 30 minutes on ice. Cell lysates were centrifuged at 15000 rpm for 20 minutes, and the extracted proteins in the supernatant were collected. After measuring the concentration of the samples using the BCA Protein Assay Kit (Thermo) and adjusting the total protein concentration to be the same for each sample, SDS-PAGE loading buffer was added and the samples were boiled for 5 minutes. Equal amounts of protein were loaded onto a 10% SDS-PAGE gel (130 V, 2.5 hours) followed by electrophoretic transfer to a nitrocellulose membrane at 4° C. (90 V, 2.5 hours). The membrane was blocked using TBST buffer (20 mM Tris pH 7.5, 150 mM NaCl, 0.1% (v/v) Tween-20) containing 5% milk proteins (Bio-Rad) at room temperature for 1 h and finally the membrane was probed with the following rabbit monoclonal antibodies: p-IKKα (Ser176)/IKKβ (Ser177) (Cell Signaling Technologies, 2071), IKKβ(Cell Signaling Technologies, 8943), IκBα (Cell Signaling Technologies, 4812), and β-Actin (Sigma, A5441). Primary antibodies were diluted according to the suggestion of the manufacturer and incubated with the nitrocellulose mem-brane overnight at 4° C. After washing, the appropriate HRP conjugated secondary antibody was added to each membrane and incubated at room temperature for 2 hours. The membrane was washed with TBST solution again and the signals were detected with the Chemiluminescent HRP Antibody Detection Reagent (Denville, E-2500) by following the manufacturer's protocol.

Concomitantly, peptide 7 increased the intracellular level of IκBα, presumably by inhibiting TNFα-induced proteasomal degradation. The same effects on NF-κB signaling had previously been reported for Antp-NBD. In agreement with the luciferase assay results (FIG. 2C), peptide 7 showed no effect on the phospho-IKKβ or IκBα level when cells were not stimulated with TNFα. Taken together, the above results indicate that peptide 7 efficiently enters the cytosol of mammalian cells and selectively inhibits the canonical NF-κB signaling pathway by blocking the NEMO-IKK interaction.

In general, peptide 7 selectively inhibits the canonical NF-κB signaling pathway but not the non-canonical NF-κB pathway. Consequently, peptide 7 inhibits the proliferation and survival of cancer cells with elevated NF-κB activities but has minimal cytotoxicity to normal cells. We have demonstrated the feasibility of designing cell-permeable bicyclic peptides whose CPP motif performs the dual function of cell penetration and target engagement. This strategy results in biologically active macrocycles that are relatively small in size and have more "drug-like" properties.

Example 3. Anticancer Activity by Bicyclic Peptidyl Inhibitors

The anticancer activity of the bicyclic peptidyl inhibitors was analyzed. Aberrant activation of NF-κB via the canonical signaling pathway plays critical roles during the initiation and progression of certain cancers. For example, NF-κB is excessively activated in ovarian cancer cell lines A2780 and CP70. Moreover, blocking canonical NF-κB activation in A2780 cells resulted in apoptosis. We therefore tested peptide 7 for potential anticancer activity against cell lines with hyperactivated NF-κB. We first examined the entry of peptide 7 into A2780 ovarian cancer cells by live-cell confocal microscopy. For confocal microscopy, A2780 cells were seeded into a glass-bottomed culture dish (MatTek) and cultured overnight at 37° C. ($5\times10^4$ cells/mL). The next day the cells were washed with DPBS (2×) and treated with 5 µM fluorescein-labeled peptide in RPMI media containing 10% FBS, and incubated at 37° C. for 2 h. The media containing the peptide was removed and the cells were washed twice with phenol-free RPMI media (2×). The cells were imaged on a Visitech Infinity 3 Hawk 2D-array live cell imaging confocal microscope equipped with a 60× oil objective.

Treatment of the cells with 5 µM FITC-labeled peptide 7 for 2 h resulted in intense green fluorescence inside all cells (FIG. 4A). Next, the effect of pep-tide 7 on the viability of A2780 and CP70 cells was assessed by a methylene blue cell viability assay. For the methylene blue cell viability assay, A2780 (2500 cells/well), CP70 (2000 cells/well) or OSE (3000 cells/well) were seeded into a 96-well microplate in 100 µL respective growth media and incubated at 37° C. overnight. The following day, the seeded cells were treated with increasing concentrations of peptide for 72 hours. The treated cells were washed with DPBS and fixed to the plate by treating with 3.7% formaldehyde solution for 1 hour. Fixation solution was removed and the fixed cells were treated with 1.0% methylene blue solution for 30 minutes. Following staining, the plate was rinsed under running water for approximately five min and left to dry. Finally, 100 µL of solubilization buffer (10% acetic acid, 50% methanol, and 40% $H_2O$) was added to each well and the absorbance was measured at 630 nm using a Tecan Infinite M1000 Pro microplate reader. Data presented were the mean±SD of five independent experiments.

Peptide 7 dose-dependently reduced the viability of both ovarian cancer cell lines, with LD50 values of about 20 and 10 μM for A2780 and CP70 cells, respectively (FIG. 4B). In contrast, peptide 7 had no significant effect on ovarian surface epithelial cells (OSE), a non-cancerous ovarian cell line with normal NF-κB activity. The greater sensitivity of CP70 cells to peptide 7 than A2780 cells is consistent with the greater dependency on NF-κB activity by the former. CP70 cells were derived from A2780 cells by subjecting the latter to low, repeated doses of cisplatin and selecting for cisplatin resistant clones. Peptide 7 also reduced the viability of A375 melanoma cells, which have constitutively activated NF-κB. The treatment of A375 cells with Antp-NBD decreased the NF-κB activity and induced growth arrest and apoptosis was previously disclosed in Ianaro et al. (Cancer Lett. 2009, 274, 331-336), which contents is incorporated by reference in its entirety.

To determine whether the observed anticancer activity of peptide 7 is correlated with specific inhibition of the NEMO-IKK interaction, we also tested the effect of peptides 1, 20, and 21 on A2780 cells by using the MTT cell viability assay. For the MTT cell viability assay, HeLa, HEK293, A2780, OSE or A375 cells were seeded into a 96-well microplate (3000 cells/well) in 100 μl of respective growth media and incubated at 37° C. overnight. The next day, a serial dilution of peptide was added to each well in 10 μL of assay medium. The treated cells were incubated at 37° C. with 5% CO2 for 72 hours. Following compound treatment, 10 μL of MTT stock solution (Roche) was added to each well. After an additional 4 h at 37° C., 100 μL of SDS-HCl solubilizing solution was added to each well and the plate was returned to the incubator overnight at 37° C. A Tecan Infinite M1000 Pro microplate reader was used the following morning to measure the absorbance of the formazan product at 565 nm. Data presented were the mean±SD of three independent experiments.

Although Antp-NBD also reduced the viability of A2780 cells in a dose-dependent manner, it was less active than peptide 7 (LD50 values of about 30 μM and >80 μM for peptide 7 and Antp-NBD, respectively; FIG. 4C). This is consistent with the fact that Antp-NBD is less potent in NEMO binding, less cell-permeable, and less metabolically stable than peptide 7. As expected, peptides 20 and 21 were also much less active than peptide 7 in this assay. Under the same conditions, none of the four peptides had significant effect on the viability of non-cancerous OSE cells (FIG. 4D). These results strongly sug-gest that the observed anticancer activity of peptide 7 (and Antp-NBD) is caused by their inhibition of the NEMO-IKK interaction and NF-κB activation.

INCORPORATION BY REFERENCE

All publications cited herein are incorporated by reference in its entirety for all purposes.

The invention claimed is:

1. A method of treating cancer in a patient, comprising administering a bicyclic polypeptide comprising Formula 5A or 5B:

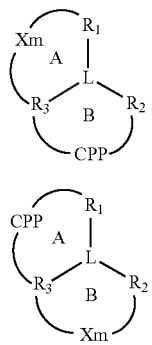

(5A)

(5B)

wherein:
CPP comprises a sequence according to Formula 2:

$$(AA_u)_m\text{-}AA_1\text{-}AA_2\text{-}AA_3\text{-}AA_4\text{-}(AA_z)_n \qquad 2$$

wherein:
each of $AA_1$, $AA_2$, $AA_3$, $AA_4$, $AA_u$, and $AA_z$ are independently selected from a D or L amino acid,
m and n are independently selected from a number from 0 to 6; and
wherein:
at least two of $AA_1$, $AA_2$, $AA_3$, $AA_4$, $AA_u$, and $AA_z$, are independently arginine, and
at least two of $AA_1$, $AA_2$, $AA_3$, $AA_4$, $AA_u$, and $AA_z$ are independently a hydrophobic amino acid;
Xm is a 4-7 amino acid sequence comprising a sequence selected from any one of GWIY (SEQ ID NO: 1), GWIYA (SEQ ID NO: 2), GWIYa (SEQ ID NO: 50), AGWIY (SEQ ID NO: 3), aGWIY (SEQ ID NO: 51), AWIYA (SEQ ID NO: 4), GAIYA (SEQ ID NO: 5), GWAYA (SEQ ID NO: 6), GWIAA (SEQ ID NO: 7), GWIYA (SEQ ID NO: 8), GAIAA (SEQ ID NO: 9), GAAAA (SEQ ID NO: 10), or the inverse of any one of the aforementioned Xm sequences (SEQ ID NOs: 52-63);
L is a linker moiety; and
each of $R_1$, $R_2$, and $R_3$ independently comprise an amide, an ester, a triazole, or a combination thereof,
wherein the cancer is diffuse large B-cell lymphoma, colon cancer, ovarian cancer, or cisplatin-resistant ovarian cancer.

2. The method of claim 1, wherein both the CPP sequence and the Xm sequence participate in binding to NEMO.

3. The method of claim 1, wherein the bicyclic polypeptide binds to the IKKα/β-binding domain on NEMO.

4. The method of claim 1, wherein the bicyclic polypeptide inhibits NEMO-IKKα/β interaction by at least about 10%.

5. The method of claim 1, wherein the bicyclic polypeptide has an IC50 of about 10 μM or less when measured for the NEMO-IKKα/β interaction.

6. The method of claim 1, wherein the bicyclic polypeptide has an IC50 of about 1.0 μM or less when measured for the NEMO-IKKα/β interaction.

7. The method of claim 1, wherein the CPP comprises a sequence according to Formula 3A-D:

$$(AA_u)_m\text{—}AA_{H2}\text{—}AA_{H1}\text{—}R\text{—}r\text{—}(AA_z)_n, \qquad \text{3-A}$$

$$(AA_u)_m\text{—}r\text{—}R\text{—}AA_{H1}\text{—}AA_{H2}\text{—}(AA_z)_n \qquad \text{3-B}$$

$$(AA_u)_m\text{—}AA_{H2}\text{—}AA_{H1}\text{—}r\text{—}R\text{—}(AA_z)_n, \text{ or} \qquad \text{3-C}$$

$$(AA_u)_m\text{—}R\text{—}r\text{—}AA_{H1}\text{—}AA_{H2}\text{—}(AA_z)_n \qquad \text{3-D}$$

wherein:
each of $AA_{H1}$ and $AA_{H2}$ are independently a hydrophobic amino acid;
each of $AA_U$ and $AA_Z$ are independently any amino acid; and
m and n are independently selected from a number from 0 to 6.

8. A method of treating cancer a patient, comprising administering a bicyclic polypeptide of Formula 5C or 5D:

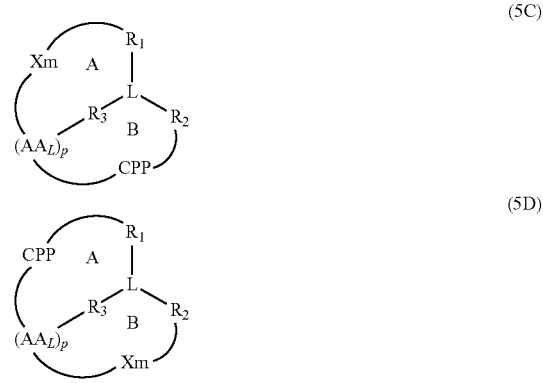

(5C)

(5D)

wherein:
CPP comprises a sequence according to Formula 2:

$$(AA_u)_m\text{-}AA_1\text{-}AA_2\text{-}AA_3\text{-}AA_4\text{-}(AA_z)_n \qquad 2$$

wherein:
each of $AA_1$, $AA_2$, $AA_3$, $AA_4$, $AA_u$ and $AA_z$ are independently selected from a D or L amino acid, and
m and n are independently selected from a number from 0 to 6; and
wherein:
at least two of $AA_1$, $AA_2$, $AA_3$, $AA_4$, $AA_u$, and $AA_z$ are independently arginine, and
at least two of $AA_1$, $AA_2$, $AA_3$, $AA_4$, $AA_u$ and $AA_z$ are independently a hydrophobic amino acid;
Xm is a 4-7 amino acid sequence comprising a sequence selected from any one of GWIY (SEQ ID NO: 1), GWIYA (SEQ ID NO: 2), GWIYa (SEQ ID NO: 50), AGWIY (SEQ ID NO: 3), aGWIY (SEQ ID NO: 51), AWIYA (SEQ ID NO: 4), GAIYA (SEQ ID NO: 5), GWAYA (SEQ ID NO: 6), GWIAA (SEQ ID NO: 7), GWIYA (SEQ ID NO: 8), GAIAA (SEQ ID NO: 9), GAAAA (SEQ ID NO: 10), or the inverse of any one of the aforementioned Xm sequences (SEQ ID NOs: 52-63);
$AA_L$ at each instance is an amino acid;
p is selected from a number from 0 to 3;
L is a linker moiety; and
each of $R_1$, $R_2$, and $R_3$ comprise an amide, an ester, a triazole, or a combination thereof, wherein the cancer is diffuse large B-cell lymphoma, colon cancer, ovarian cancer, or cisplatin-resistant ovarian cancer.

9. The method of claim 8, wherein both the CPP sequence and the Xm sequence participate in binding to NEMO.

10. The method of claim 8, wherein the bicyclic polypeptide binds to the IKKα/β-binding domain on NEMO.

11. The method of claim 8, wherein the bicyclic polypeptide inhibits NEMO-IKKα/β interaction by at least about 10%.

12. The method of claim 8, wherein the bicyclic polypeptide has an IC50 of about 10 μM or less when measured for the NEMO-IKKα/β interaction.

13. The method of claim 8, wherein the bicyclic polypeptide has an IC50 of about 1.0 μM or less when measured for the NEMO-IKKα/β interaction.

14. The method of claim 8, wherein the CPP comprises a sequence according to Formula 3A-D:

$$(AA_u)_m - AA_{H2} - AA_{H1} - R - r - (AA_z)_n, \quad \text{3-A}$$

$$(AA_u)_m - r - R - AA_{H1} - AA_{H2} - (AA_z)_n \quad \text{3-B}$$

$$(AA_u)_m - AA_{H2} - AA_{H1} - r - R - (AA_z)_n, \text{ or} \quad \text{3-C}$$

$$(AA_u)_m - R - r - AA_{H1} - AA_{H2} - (AA_z)_n \quad \text{3-D}$$

wherein:
 each of $AA_{H1}$ and $AA_{H2}$ are independently a hydrophobic amino acid;
 each of $AA_U$ and $AA_Z$ are independently any amino acid; and
 m and n are independently selected from a number from 0 to 6.

* * * * *

SEQUENCE LISTING

```
<160> NUMBER OF SEQ ID NOS: 158

<210> SEQ ID NO 1
<211> LENGTH: 4
<212> TYPE: PRT
<213> ORGANISM: Artificial Sequence
<220> FEATURE:
<223> OTHER INFORMATION: synthetic construct

<400> SEQUENCE: 1

Gly Trp Ile Tyr
1

<210> SEQ ID NO 2
<211> LENGTH: 5
<212> TYPE: PRT
<213> ORGANISM: Artificial Sequence
<220> FEATURE:
<223> OTHER INFORMATION: synthetic construct

<400> SEQUENCE: 2

Gly Trp Ile Tyr Ala
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic construct

<400> SEQUENCE: 3

Ala Gly Trp Ile Tyr
1               5

<210> SEQ ID NO 4
```

```
<211> LENGTH: 5
<212> TYPE: PRT
<213> ORGANISM: Artificial Sequence
<220> FEATURE:
<223> OTHER INFORMATION: synthetic construct

<400> SEQUENCE: 4

Ala Trp Ile Tyr Ala
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic construct

<400> SEQUENCE: 5

Gly Ala Ile Tyr Ala
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic construct

<400> SEQUENCE: 6

Gly Trp Ala Tyr Ala
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic construct

<400> SEQUENCE: 7

Gly Trp Ile Ala Ala
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic construct

<400> SEQUENCE: 8

Gly Trp Ile Tyr Ala
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic construct

<400> SEQUENCE: 9

Gly Ala Ile Ala Ala
1               5

<210> SEQ ID NO 10
<211> LENGTH: 5
```

```
<212> TYPE: PRT
<213> ORGANISM: Artificial Sequence
<220> FEATURE:
<223> OTHER INFORMATION: synthetic construct

<400> SEQUENCE: 10

Gly Ala Ala Ala Ala
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic construct

<400> SEQUENCE: 11

Cys Arg Arg Arg Arg Phe Trp
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: selenocysteine

<400> SEQUENCE: 12

Xaa Arg Arg Arg Arg Phe Trp
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic construct

<400> SEQUENCE: 13

Cys Arg Arg Arg Arg Phe Trp
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic construct

<400> SEQUENCE: 14

Phe Trp Arg Arg Arg
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic construct

<400> SEQUENCE: 15

Arg Arg Arg Trp Phe
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: synthetic construct

<400> SEQUENCE: 16

Phe Phe Arg Arg Arg
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic construct

<400> SEQUENCE: 17

Phe Arg Phe Arg Arg
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic construct

<400> SEQUENCE: 18

Phe Arg Arg Phe Arg
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic construct

<400> SEQUENCE: 19

Phe Arg Arg Arg Phe
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic construct

<400> SEQUENCE: 20

Phe Phe Phe Arg Ala
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic construct

<400> SEQUENCE: 21

Phe Phe Phe Arg Arg
1               5
```

```
<210> SEQ ID NO 22
<211> LENGTH: 6
<212> TYPE: PRT
<213> ORGANISM: Artificial Sequence
<220> FEATURE:
<223> OTHER INFORMATION: synthetic construct

<400> SEQUENCE: 22

Phe Phe Arg Arg Arg Arg
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic construct

<400> SEQUENCE: 23

Phe Arg Arg Phe Arg Arg
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic construct

<400> SEQUENCE: 24

Phe Arg Arg Arg Phe Arg
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic construct

<400> SEQUENCE: 25

Arg Phe Phe Arg Arg Arg
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic construct

<400> SEQUENCE: 26

Arg Phe Arg Arg Phe Arg
1               5

<210> SEQ ID NO 27
<211> LENGTH: 6
<212> TYPE: PRT
<213> ORGANISM: Artificial Sequence
<220> FEATURE:
<223> OTHER INFORMATION: synthetic construct

<400> SEQUENCE: 27

Phe Arg Phe Arg Arg Arg
1               5

<210> SEQ ID NO 28
```

```
<211> LENGTH: 6
<212> TYPE: PRT
<213> ORGANISM: Artificial Sequence
<220> FEATURE:
<223> OTHER INFORMATION: synthetic construct

<400> SEQUENCE: 28

Phe Phe Phe Arg Arg Arg
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic construct

<400> SEQUENCE: 29

Phe Phe Arg Arg Arg Phe
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic construct

<400> SEQUENCE: 30

Phe Arg Phe Phe Arg Arg
1               5

<210> SEQ ID NO 31
<211> LENGTH: 6
<212> TYPE: PRT
<213> ORGANISM: Artificial Sequence
<220> FEATURE:
<223> OTHER INFORMATION: synthetic construct

<400> SEQUENCE: 31

Arg Arg Phe Phe Phe Arg
1               5

<210> SEQ ID NO 32
<211> LENGTH: 6
<212> TYPE: PRT
<213> ORGANISM: Artificial Sequence
<220> FEATURE:
<223> OTHER INFORMATION: synthetic construct

<400> SEQUENCE: 32

Phe Phe Arg Phe Arg Arg
1               5

<210> SEQ ID NO 33
<211> LENGTH: 6
<212> TYPE: PRT
<213> ORGANISM: Artificial Sequence
<220> FEATURE:
<223> OTHER INFORMATION: synthetic construct

<400> SEQUENCE: 33

Phe Phe Arg Arg Phe Arg
1               5

<210> SEQ ID NO 34
<211> LENGTH: 6
```

```
<212> TYPE: PRT
<213> ORGANISM: Artificial Sequence
<220> FEATURE:
<223> OTHER INFORMATION: synthetic construct

<400> SEQUENCE: 34

Phe Arg Arg Phe Phe Arg
1               5

<210> SEQ ID NO 35
<211> LENGTH: 6
<212> TYPE: PRT
<213> ORGANISM: Artificial Sequence
<220> FEATURE:
<223> OTHER INFORMATION: synthetic construct

<400> SEQUENCE: 35

Phe Arg Arg Phe Arg Phe
1               5

<210> SEQ ID NO 36
<211> LENGTH: 6
<212> TYPE: PRT
<213> ORGANISM: Artificial Sequence
<220> FEATURE:
<223> OTHER INFORMATION: synthetic construct

<400> SEQUENCE: 36

Phe Arg Phe Arg Phe Arg
1               5

<210> SEQ ID NO 37
<211> LENGTH: 6
<212> TYPE: PRT
<213> ORGANISM: Artificial Sequence
<220> FEATURE:
<223> OTHER INFORMATION: synthetic construct

<400> SEQUENCE: 37

Arg Phe Phe Arg Phe Arg
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic construct

<400> SEQUENCE: 38

Phe Phe Phe Arg Arg Arg Arg
1               5

<210> SEQ ID NO 39
<211> LENGTH: 7
<212> TYPE: PRT
<213> ORGANISM: Artificial Sequence
<220> FEATURE:
<223> OTHER INFORMATION: synthetic construct

<400> SEQUENCE: 39

Arg Phe Phe Arg Arg Arg Arg
1               5

<210> SEQ ID NO 40
<211> LENGTH: 7
<212> TYPE: PRT
```

```
<213> ORGANISM: Artificial Sequence
<220> FEATURE:
<223> OTHER INFORMATION: synthetic construct

<400> SEQUENCE: 40

Arg Arg Phe Phe Arg Arg Arg
1               5

<210> SEQ ID NO 41
<211> LENGTH: 7
<212> TYPE: PRT
<213> ORGANISM: Artificial Sequence
<220> FEATURE:
<223> OTHER INFORMATION: synthetic construct

<400> SEQUENCE: 41

Arg Phe Phe Phe Arg Arg Arg
1               5

<210> SEQ ID NO 42
<211> LENGTH: 7
<212> TYPE: PRT
<213> ORGANISM: Artificial Sequence
<220> FEATURE:
<223> OTHER INFORMATION: synthetic construct

<400> SEQUENCE: 42

Arg Arg Phe Phe Phe Arg Arg
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic construct

<400> SEQUENCE: 43

Phe Phe Arg Arg Phe Arg Arg
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic construct

<400> SEQUENCE: 44

Phe Phe Arg Arg Arg Arg Phe
1               5

<210> SEQ ID NO 45
<211> LENGTH: 7
<212> TYPE: PRT
<213> ORGANISM: Artificial Sequence
<220> FEATURE:
<223> OTHER INFORMATION: synthetic construct

<400> SEQUENCE: 45

Phe Arg Arg Phe Phe Arg Arg
1               5

<210> SEQ ID NO 46
<211> LENGTH: 8
<212> TYPE: PRT
<213> ORGANISM: Artificial Sequence
```

```
<220> FEATURE:
<223> OTHER INFORMATION: synthetic construct

<400> SEQUENCE: 46

Phe Phe Phe Arg Arg Arg Arg Arg
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic construct

<400> SEQUENCE: 47

Phe Phe Phe Arg Arg Arg Arg Arg Arg
1               5

<210> SEQ ID NO 48
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(2)
<223> OTHER INFORMATION: Xaa is any amino acid

<400> SEQUENCE: 48

Xaa Xaa Arg Arg Arg Arg
1               5

<210> SEQ ID NO 49
<211> LENGTH: 8
<212> TYPE: PRT
<213> ORGANISM: Artificial Sequence
<220> FEATURE:
<223> OTHER INFORMATION: synthetic construct

<400> SEQUENCE: 49

Trp Arg Trp Arg Trp Arg Trp Arg
1               5

<210> SEQ ID NO 50
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: D-alanine

<400> SEQUENCE: 50

Gly Trp Ile Tyr Ala
1               5

<210> SEQ ID NO 51
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-alanine
```

```
<400> SEQUENCE: 51

Ala Gly Trp Ile Tyr
1               5

<210> SEQ ID NO 52
<211> LENGTH: 4
<212> TYPE: PRT
<213> ORGANISM: Artificial Sequence
<220> FEATURE:
<223> OTHER INFORMATION: synthetic construct

<400> SEQUENCE: 52

Tyr Ile Trp Gly
1

<210> SEQ ID NO 53
<211> LENGTH: 5
<212> TYPE: PRT
<213> ORGANISM: Artificial Sequence
<220> FEATURE:
<223> OTHER INFORMATION: synthetic construct

<400> SEQUENCE: 53

Ala Tyr Ile Trp Gly
1               5

<210> SEQ ID NO 54
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-alanine

<400> SEQUENCE: 54

Ala Tyr Ile Trp Gly
1               5

<210> SEQ ID NO 55
<211> LENGTH: 5
<212> TYPE: PRT
<213> ORGANISM: Artificial Sequence
<220> FEATURE:
<223> OTHER INFORMATION: synthetic construct

<400> SEQUENCE: 55

Tyr Ile Trp Gly Ala
1               5

<210> SEQ ID NO 56
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: D-alanine

<400> SEQUENCE: 56

Tyr Ile Trp Gly Ala
1               5
```

```
<210> SEQ ID NO 57
<211> LENGTH: 5
<212> TYPE: PRT
<213> ORGANISM: Artificial Sequence
<220> FEATURE:
<223> OTHER INFORMATION: synthetic construct

<400> SEQUENCE: 57

Ala Tyr Ile Trp Ala
1               5

<210> SEQ ID NO 58
<211> LENGTH: 5
<212> TYPE: PRT
<213> ORGANISM: Artificial Sequence
<220> FEATURE:
<223> OTHER INFORMATION: synthetic construct

<400> SEQUENCE: 58

Ala Tyr Ile Ala Gly
1               5

<210> SEQ ID NO 59
<211> LENGTH: 5
<212> TYPE: PRT
<213> ORGANISM: Artificial Sequence
<220> FEATURE:
<223> OTHER INFORMATION: synthetic construct

<400> SEQUENCE: 59

Ala Tyr Ala Trp Gly
1               5

<210> SEQ ID NO 60
<211> LENGTH: 5
<212> TYPE: PRT
<213> ORGANISM: Artificial Sequence
<220> FEATURE:
<223> OTHER INFORMATION: synthetic construct

<400> SEQUENCE: 60

Ala Ala Ile Trp Gly
1               5

<210> SEQ ID NO 61
<211> LENGTH: 5
<212> TYPE: PRT
<213> ORGANISM: Artificial Sequence
<220> FEATURE:
<223> OTHER INFORMATION: synthetic construct

<400> SEQUENCE: 61

Ala Tyr Ile Trp Gly
1               5

<210> SEQ ID NO 62
<211> LENGTH: 5
<212> TYPE: PRT
<213> ORGANISM: Artificial Sequence
<220> FEATURE:
<223> OTHER INFORMATION: synthetic construct

<400> SEQUENCE: 62

Ala Ala Ile Ala Gly
1               5
```

```
<210> SEQ ID NO 63
<211> LENGTH: 5
<212> TYPE: PRT
<213> ORGANISM: Artificial Sequence
<220> FEATURE:
<223> OTHER INFORMATION: synthetic construct

<400> SEQUENCE: 63

Ala Ala Ala Ala Gly
1               5

<210> SEQ ID NO 64
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(10)
<223> OTHER INFORMATION: Xaa is glycine, D-glycine, tryptophan,
      D-tryptophan, isoleucine, D-isoleucine, tyrosine, D-tyrosine,
      alanine or D-alanine
<220> FEATURE:
<221> NAME/KEY: SITE
<222> LOCATION: (4)..(10)
<223> OTHER INFORMATION: Individual residues may be present or absent

<400> SEQUENCE: 64

Xaa Xaa Xaa Xaa Xaa Xaa Xaa Xaa Xaa Xaa
1               5                   10

<210> SEQ ID NO 65
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(7)
<223> OTHER INFORMATION: cyclic peptide
<220> FEATURE:
<221> NAME/KEY: MOD_RES
<222> LOCATION: (2)..(2)
<223> OTHER INFORMATION: Xaa is napthylalanine

<400> SEQUENCE: 65

Phe Xaa Arg Arg Arg Arg Gln
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 66

Phe Xaa Arg Arg Arg
1               5

<210> SEQ ID NO 67
<211> LENGTH: 6
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 67

Phe Xaa Arg Arg Arg Cys
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (6)..(6)
<223> OTHER INFORMATION: Selenocysteine

<400> SEQUENCE: 68

Phe Xaa Arg Arg Arg Xaa
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-2-naphthylalanine

<400> SEQUENCE: 69

Arg Arg Arg Xaa Phe
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 70

Arg Arg Arg Arg Xaa Phe
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 71
```

```
Phe Xaa Arg Arg Arg Arg
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-2-naphthylalanine
<220> FEATURE:
<221> NAME/KEY: MOD_RES
<222> LOCATION: (3)..(3)
<223> OTHER INFORMATION: D-arginine
<220> FEATURE:
<221> NAME/KEY: MOD_RES
<222> LOCATION: (5)..(5)
<223> OTHER INFORMATION: D-arginine

<400> SEQUENCE: 72

Phe Xaa Arg Arg Arg Arg
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 73

Phe Xaa Arg Arg Arg Arg
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 74

Arg Arg Phe Arg Xaa Arg
1               5

<210> SEQ ID NO 75
<211> LENGTH: 6
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-2-naphthylalanine

<400> SEQUENCE: 75

Phe Arg Arg Arg Arg Xaa
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-arginine
<220> FEATURE:
<221> NAME/KEY: MOD_RES
<222> LOCATION: (5)..(5)
<223> OTHER INFORMATION: L-2-naphthylalanine

<400> SEQUENCE: 76

Arg Arg Phe Arg Xaa Arg
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-2-naphthylalanine

<400> SEQUENCE: 77

Arg Arg Xaa Phe Arg Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-phenylalanine
<220> FEATURE:
<221> NAME/KEY: MOD_RES
<222> LOCATION: (3)..(3)
<223> OTHER INFORMATION: L-2-naphthylalanine
<220> FEATURE:
<221> NAME/KEY: MOD_RES
<222> LOCATION: (5)..(5)
<223> OTHER INFORMATION: D-arginine
<220> FEATURE:
<221> NAME/KEY: MOD_RES
<222> LOCATION: (7)..(7)
<223> OTHER INFORMATION: D-arginine

<400> SEQUENCE: 78

Phe Phe Xaa Arg Arg Arg Arg
1               5
```

<210> SEQ ID NO 79
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-2-naphthylalanine

<400> SEQUENCE: 79

Phe Phe Xaa Arg Arg Arg Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-2-naphthylalanine

<400> SEQUENCE: 80

Arg Phe Arg Phe Arg Xaa Arg
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 81

Phe Xaa Arg Arg Arg Arg Gln Lys
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 82

Phe Xaa Arg Arg Arg Arg Gln Cys
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)

```
<223> OTHER INFORMATION: D-phenylalanine
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 83

Phe Xaa Arg Arg Arg Arg Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 84

Phe Xaa Arg Arg Arg Arg Arg
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine
<220> FEATURE:
<221> NAME/KEY: MOD_RES
<222> LOCATION: (8)..(8)
<223> OTHER INFORMATION: L-norleucine

<400> SEQUENCE: 85

Arg Arg Arg Arg Xaa Phe Asp Xaa Cys
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: D-arginine
<220> FEATURE:
<221> NAME/KEY: MOD_RES
<222> LOCATION: (5)..(5)
<223> OTHER INFORMATION: D-arginine

<400> SEQUENCE: 86

Phe Phe Arg Arg Arg
1               5
```

```
<210> SEQ ID NO 87
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: D-arginine

<400> SEQUENCE: 87

Phe Phe Arg Arg Arg
1               5

<210> SEQ ID NO 88
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 88

Gly Xaa Arg Arg Arg
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 89

Gly Xaa Arg Arg Arg Arg
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 90

Phe Xaa Arg Arg Arg Arg
1               5

<210> SEQ ID NO 91
<211> LENGTH: 6
<212> TYPE: PRT
```

<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-phenylalanine
<220> FEATURE:
<221> NAME/KEY: MOD_RES
<222> LOCATION: (5)..(5)
<223> OTHER INFORMATION: D-arginine

<400> SEQUENCE: 91

Phe Phe Phe Arg Arg Arg
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MOD_RES
<222> LOCATION: (3)..(3)
<223> OTHER INFORMATION: D-phenylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 92

Phe Phe Phe Arg Arg Arg
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MOD_RES
<222> LOCATION: (3)..(3)
<223> OTHER INFORMATION: D-phenylalanine
<220> FEATURE:
<221> NAME/KEY: MOD_RES
<222> LOCATION: (5)..(5)
<223> OTHER INFORMATION: D-arginine

<400> SEQUENCE: 93

Phe Phe Phe Arg Arg Arg
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: (2)..(2)
<223> OTHER INFORMATION: D-phenylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 94

Phe Phe Phe Arg Arg Arg
1               5

<210> SEQ ID NO 95
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MOD_RES
<222> LOCATION: (3)..(3)
<223> OTHER INFORMATION: D-2-naphthylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 95

Phe Phe Xaa Arg Arg Arg
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-phenylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 96

Phe Xaa Phe Arg Arg Arg
1               5
```

```
<210> SEQ ID NO 97
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-2-naphthylalanine
<220> FEATURE:
<221> NAME/KEY: MOD_RES
<222> LOCATION: (3)..(3)
<223> OTHER INFORMATION: D-phenylalanine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine

<400> SEQUENCE: 97

Xaa Phe Phe Arg Arg Arg
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-arginine
<220> FEATURE:
<221> NAME/KEY: MOD_RES
<222> LOCATION: (5)..(5)
<223> OTHER INFORMATION: D-arginine

<400> SEQUENCE: 98

Phe Xaa Arg Arg Arg
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-arginine
<220> FEATURE:
<221> NAME/KEY: MOD_RES
<222> LOCATION: (5)..(5)
<223> OTHER INFORMATION: D-arginine

<400> SEQUENCE: 99
```

```
Phe Xaa Arg Arg Arg
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: D-phenylalanine
<220> FEATURE:
<221> NAME/KEY: MOD_RES
<222> LOCATION: (5)..(5)
<223> OTHER INFORMATION: D-arginine
<220> FEATURE:
<221> NAME/KEY: MOD_RES
<222> LOCATION: (7)..(7)
<223> OTHER INFORMATION: D-arginine

<400> SEQUENCE: 100

Lys Phe Phe Arg Arg Arg Arg Asp
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: L-2,3-diaminopropionic acid
<220> FEATURE:
<221> NAME/KEY: MOD_RES
<222> LOCATION: (2)..(2)
<223> OTHER INFORMATION: D-phenylalanine
<220> FEATURE:
<221> NAME/KEY: MOD_RES
<222> LOCATION: (5)..(5)
<223> OTHER INFORMATION: D-arginine
<220> FEATURE:
<221> NAME/KEY: MOD_RES
<222> LOCATION: (7)..(7)
<223> OTHER INFORMATION: D-arginine

<400> SEQUENCE: 101

Xaa Phe Phe Arg Arg Arg Arg Asp
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(8)
<223> OTHER INFORMATION: disulfide bond

<400> SEQUENCE: 102
```

```
Cys Trp Trp Arg Arg Arg Arg Cys
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(9)
<223> OTHER INFORMATION: disulfide bond

<400> SEQUENCE: 103

Cys Trp Trp Trp Arg Arg Arg Arg Cys
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(8)
<223> OTHER INFORMATION: disulfide bond

<400> SEQUENCE: 104

Cys Phe Trp Arg Arg Arg Arg Cys
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(8)
<223> OTHER INFORMATION: disulfide bond

<400> SEQUENCE: 105

Cys Trp Trp Trp Arg Arg Arg Cys
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(6)
<223> OTHER INFORMATION: D-arginine
<220> FEATURE:
<221> NAME/KEY: MOD_RES
<222> LOCATION: (7)..(7)
<223> OTHER INFORMATION: D-glutamate
```

```
<400> SEQUENCE: 106

Xaa Xaa Arg Glu Arg Arg Glu
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(6)
<223> OTHER INFORMATION: D-arginine
<220> FEATURE:
<221> NAME/KEY: MOD_RES
<222> LOCATION: (7)..(7)
<223> OTHER INFORMATION: D-glutamate

<400> SEQUENCE: 107

Xaa Xaa Arg Arg Arg Arg Glu
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(3)
<223> OTHER INFORMATION: L-2-naphthylalanine
<220> FEATURE:
<221> NAME/KEY: MOD_RES
<222> LOCATION: (5)..(6)
<223> OTHER INFORMATION: D-arginine
<220> FEATURE:
<221> NAME/KEY: MOD_RES
<222> LOCATION: (7)..(7)
<223> OTHER INFORMATION: D-glutamate

<400> SEQUENCE: 108

Xaa Xaa Xaa Arg Arg Arg Glu
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(3)
<223> OTHER INFORMATION: L-2-naphthylalanine
<220> FEATURE:
```

```
<221> NAME/KEY: MOD_RES
<222> LOCATION: (5)..(6)
<223> OTHER INFORMATION: D-arginine

<400> SEQUENCE: 109

Xaa Xaa Xaa Arg Arg Arg Glu
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(6)
<223> OTHER INFORMATION: D-arginine
<220> FEATURE:
<221> NAME/KEY: MOD_RES
<222> LOCATION: (7)..(7)
<223> OTHER INFORMATION: D-glutamate

<400> SEQUENCE: 110

Xaa Xaa Phe Arg Arg Arg Glu
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(6)
<223> OTHER INFORMATION: D-arginine

<400> SEQUENCE: 111

Xaa Xaa Phe Arg Arg Arg Glu
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
```

```
<221> NAME/KEY: MOD_RES
<222> LOCATION: (3)..(3)
<223> OTHER INFORMATION: D-phenylalanine
<220> FEATURE:
<221> NAME/KEY: MOD_RES
<222> LOCATION: (5)..(6)
<223> OTHER INFORMATION: D-arginine
<220> FEATURE:
<221> NAME/KEY: MOD_RES
<222> LOCATION: (7)..(7)
<223> OTHER INFORMATION: D-glutamate

<400> SEQUENCE: 112

Xaa Xaa Phe Arg Arg Arg Glu
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-phenylalanine
<220> FEATURE:
<221> NAME/KEY: MOD_RES
<222> LOCATION: (5)..(6)
<223> OTHER INFORMATION: D-arginine

<400> SEQUENCE: 113

Xaa Xaa Phe Arg Arg Arg Glu
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-2-naphthylalanine
<220> FEATURE:
<221> NAME/KEY: MOD_RES
<222> LOCATION: (5)..(6)
<223> OTHER INFORMATION: D-arginine

<400> SEQUENCE: 114

Xaa Xaa Xaa Arg Arg Arg Glu
1               5

<210> SEQ ID NO 115
<211> LENGTH: 7
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-2-naphthylalanine
<220> FEATURE:
<221> NAME/KEY: MOD_RES
<222> LOCATION: (5)..(6)
<223> OTHER INFORMATION: D-arginine
<220> FEATURE:
<221> NAME/KEY: MOD_RES
<222> LOCATION: (7)..(7)
<223> OTHER INFORMATION: D-glutamate

<400> SEQUENCE: 115

Xaa Xaa Xaa Arg Arg Arg Glu
1               5

<210> SEQ ID NO 116
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Arg is modified with pimelic acid
<220> FEATURE:
<221> NAME/KEY: SITE
<222> LOCATION: (1)..(4)
<223> OTHER INFORMATION: Cyclization between Arg is modified with
      pimelic acid and Arg is modified with lysine peptoid residue
<220> FEATURE:
<221> NAME/KEY: MOD_RES
<222> LOCATION: (4)..(4)
<223> OTHER INFORMATION: Arg is modified with lysine peptoid residue

<400> SEQUENCE: 116

Arg Gln Arg Arg Gly Arg Arg Arg
1               5

<210> SEQ ID NO 117
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (2)..(19)
<223> OTHER INFORMATION: Cys residues jopined by disulfide bond

<400> SEQUENCE: 117

Lys Cys Phe Gln Trp Gln Arg Asn Met Arg Lys Val Arg Gly Pro Pro
1               5                  10                  15

Val Ser Cys

<210> SEQ ID NO 118
<211> LENGTH: 11
<212> TYPE: PRT
<213> ORGANISM: Artificial Sequence
```

```
<220> FEATURE:
<223> OTHER INFORMATION: synthetic construct
<220> FEATURE:
<221> NAME/KEY: SITE
<222> LOCATION: (1)..(11)
<223> OTHER INFORMATION: Cyclization between Lys and Glu
<220> FEATURE:
<221> NAME/KEY: MOD_RES
<222> LOCATION: (2)..(2)
<223> OTHER INFORMATION: D-arginine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (10)..(10)
<223> OTHER INFORMATION: D-arginine

<400> SEQUENCE: 118

Lys Arg Arg Arg Gly Arg Lys Lys Arg Arg Glu
1               5                   10

<210> SEQ ID NO 119
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(12)
<223> OTHER INFORMATION: Cyclization between Lys and Glu
<220> FEATURE:
<221> NAME/KEY: MOD_RES
<222> LOCATION: (2)..(2)
<223> OTHER INFORMATION: D-arginine
<220> FEATURE:
<221> NAME/KEY: MOD_RES
<222> LOCATION: (4)..(4)
<223> OTHER INFORMATION: D-arginine
<220> FEATURE:
<221> NAME/KEY: MOD_RES
<222> LOCATION: (6)..(6)
<223> OTHER INFORMATION: D-arginine
<220> FEATURE:
<221> NAME/KEY: MOD_RES
<222> LOCATION: (8)..(8)
<223> OTHER INFORMATION: D-arginine
<220> FEATURE:
<221> NAME/KEY: MOD_RES
<222> LOCATION: (10)..(10)
<223> OTHER INFORMATION: D-arginine

<400> SEQUENCE: 119

Lys Arg Arg Arg Arg Arg Arg Arg Arg Arg Arg Glu
1               5                   10

<210> SEQ ID NO 120
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (13)..(13)
```

<223> OTHER INFORMATION: D-proline

<400> SEQUENCE: 120

Arg Val Arg Thr Arg Gly Lys Arg Arg Ile Arg Pro Pro
1               5                   10

<210> SEQ ID NO 121
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (13)..(13)
<223> OTHER INFORMATION: D-proline

<400> SEQUENCE: 121

Arg Thr Arg Thr Arg Gly Lys Arg Arg Ile Arg Val Pro Pro
1               5                   10

<210> SEQ ID NO 122
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (4)..(21)
<223> OTHER INFORMATION: Cys residues jopined by disulfide bond
<220> FEATURE:
<221> NAME/KEY: DISULFID
<222> LOCATION: (11)..(23)
<223> OTHER INFORMATION: Cys residues jopined by disulfide bond
<220> FEATURE:
<221> NAME/KEY: DISULFID
<222> LOCATION: (17)..(29)
<223> OTHER INFORMATION: Cys residues jopined by disulfide bond

<400> SEQUENCE: 122

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 123
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(10)
<223> OTHER INFORMATION: Macrocyclization by multicomponent reaction
      with aziridine aldehyde and isocyanide
<220> FEATURE:
<221> NAME/KEY: MOD_RES
<222> LOCATION: (2)..(2)
<223> OTHER INFORMATION: L-3-cyclohexyl-alanine
<220> FEATURE:
<221> NAME/KEY: MOD_RES
<222> LOCATION: (3)..(3)
<223> OTHER INFORMATION: D-arginine
<220> FEATURE:
<221> NAME/KEY: MOD_RES
<222> LOCATION: (4)..(4)
<223> OTHER INFORMATION: L-cyclohexylalanine
<220> FEATURE:

```
<221> NAME/KEY: MOD_RES
<222> LOCATION: (5)..(5)
<223> OTHER INFORMATION: D-arginine
<220> FEATURE:
<221> NAME/KEY: MOD_RES
<222> LOCATION: (6)..(6)
<223> OTHER INFORMATION: L-cyclohexylalanine
<220> FEATURE:
<221> NAME/KEY: MOD_RES
<222> LOCATION: (7)..(7)
<223> OTHER INFORMATION: D-arginine
<220> FEATURE:
<221> NAME/KEY: MOD_RES
<222> LOCATION: (8)..(8)
<223> OTHER INFORMATION: L-cyclohexylalanine
<220> FEATURE:
<221> NAME/KEY: MOD_RES
<222> LOCATION: (9)..(9)
<223> OTHER INFORMATION: D-arginine

<400> SEQUENCE: 123

Pro Xaa Arg Xaa Arg Xaa Arg Xaa Arg Gly
1               5                   10

<210> SEQ ID NO 124
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ser is modified with trimesic acid
<220> FEATURE:
<221> NAME/KEY: SITE
<222> LOCATION: (1)..(13)
<223> OTHER INFORMATION: N-terminal amine and side chains of two
     L-2,3-diaminopropionic acid residues bicyclized with trimesic acid
<220> FEATURE:
<221> NAME/KEY: MOD_RES
<222> LOCATION: (2)..(2)
<223> OTHER INFORMATION: D-valine
<220> FEATURE:
<221> NAME/KEY: MOD_RES
<222> LOCATION: (4)..(4)
<223> OTHER INFORMATION: L-4-(phosphonodifluoromethyl)phenylalanine
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-naphthylalanine
<220> FEATURE:
<221> NAME/KEY: MOD_RES
<222> LOCATION: (13)..(13)
<223> OTHER INFORMATION: L-2,3-diaminopropionic acid

<400> SEQUENCE: 124

Ser Val Pro Xaa His Xaa Phe Xaa Arg Arg Arg Arg Xaa
1               5                   10

<210> SEQ ID NO 125
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-alanine is modified with trimesic acid
<220> FEATURE:
```

```
<221> NAME/KEY: MOD_RES
<222> LOCATION: (1)..(1)
<223> OTHER INFORMATION: D-amino acid
<220> FEATURE:
<221> NAME/KEY: SITE
<222> LOCATION: (1)..(17)
<223> OTHER INFORMATION: N-terminal amine and side chains of two
      L-2,3-diaminopropionic acid residues bicyclized with trimesic acid
<220> FEATURE:
<221> NAME/KEY: MOD_RES
<222> LOCATION: (2)..(2)
<223> OTHER INFORMATION: sarcosine
<220> FEATURE:
<221> NAME/KEY: MOD_RES
<222> LOCATION: (4)..(4)
<223> OTHER INFORMATION: D-phosphothreonine
<220> FEATURE:
<221> NAME/KEY: MOD_RES
<222> LOCATION: (5)..(5)
<223> OTHER INFORMATION: L-homoproline
<220> FEATURE:
<221> NAME/KEY: MOD_RES
<222> LOCATION: (6)..(6)
<223> OTHER INFORMATION: L-naphthylalanine
<220> FEATURE:
<221> NAME/KEY: MOD_RES
<222> LOCATION: (9)..(9)
<223> OTHER INFORMATION: D-alanine
<220> FEATURE:
<221> NAME/KEY: MOD_RES
<222> LOCATION: (10)..(10)
<223> OTHER INFORMATION: L-2,3-diaminopropionic acid
<220> FEATURE:
<221> NAME/KEY: MOD_RES
<222> LOCATION: (12)..(12)
<223> OTHER INFORMATION: L-naphthylalanine
<220> FEATURE:
<221> NAME/KEY: MOD_RES
<222> LOCATION: (17)..(17)
<223> OTHER INFORMATION: L-2,3-diaminopropionic acid

<400> SEQUENCE: 125

Ala Xaa Asp Xaa Xaa Xaa Arg Ala Xaa Xaa Phe Xaa Arg Arg Arg Arg
1               5                   10                  15

Xaa

<210> SEQ ID NO 126
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(15)
<223> OTHER INFORMATION: Three Cys side chains bicyclized with
      tris(bromomethyl)benzene

<400> SEQUENCE: 126

Cys Arg Arg Ser Arg Arg Gly Cys Gly Arg Arg Ser Arg Arg Cys Gly
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(15)
<223> OTHER INFORMATION: Three Cys side chains bicyclized with
      tris(bromomethyl)benzene
```

```
<400> SEQUENCE: 127

Cys Arg Arg Ser Arg Arg Gly Cys Gly Arg Arg Ser Arg Arg Cys Gly
1               5                   10                  15

<210> SEQ ID NO 128
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (1)..(2)
<223> OTHER INFORMATION: linked by dodecanoyl moiety

<400> SEQUENCE: 128

Lys Arg Arg Arg Arg
1               5

<210> SEQ ID NO 129
<211> LENGTH: 16
<212> TYPE: PRT
<213> ORGANISM: Artificial Sequence
<220> FEATURE:
<223> OTHER INFORMATION: synthetic construct

<400> SEQUENCE: 129

Leu Lys Lys Leu Cys Lys Leu Leu Lys Lys Leu Cys Lys Leu Ala Gly
1               5                   10                  15

<210> SEQ ID NO 130
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (5)..(9)
<223> OTHER INFORMATION: Cyclization between Lys and Glu

<400> SEQUENCE: 130

Arg Arg Arg Arg Lys Arg Arg Arg Glu
1               5

<210> SEQ ID NO 131
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (4)..(9)
<223> OTHER INFORMATION: Cyclization between Lys and Glu

<400> SEQUENCE: 131

Arg Arg Arg Lys Arg Arg Arg Arg Glu
1               5

<210> SEQ ID NO 132
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (3)..(9)
```

```
<223> OTHER INFORMATION: Cyclization between Lys and Glu

<400> SEQUENCE: 132

Arg Arg Lys Arg Arg Arg Arg Glu
1               5

<210> SEQ ID NO 133
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (2)..(9)
<223> OTHER INFORMATION: Cyclization between Lys and Glu

<400> SEQUENCE: 133

Arg Lys Arg Arg Arg Arg Arg Arg Glu
1               5

<210> SEQ ID NO 134
<211> LENGTH: 8
<212> TYPE: PRT
<213> ORGANISM: Artificial Sequence
<220> FEATURE:
<223> OTHER INFORMATION: synthetic construct

<400> SEQUENCE: 134

Cys Arg Cys Arg Cys Arg Cys Arg
1               5

<210> SEQ ID NO 135
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: SITE
<222> LOCATION: (1)..(12)
<223> OTHER INFORMATION: Cyclization by the click reaction between
      L-propargylglycine and L-6-Azido-2-amino-hexanoic
<220> FEATURE:
<221> NAME/KEY: MOD_RES
<222> LOCATION: (12)..(12)
<223> OTHER INFORMATION: L-6-Azido-2-amino-hexanoic

<400> SEQUENCE: 135

Xaa Leu Arg Lys Arg Leu Arg Lys Phe Arg Asn Xaa
1               5                   10

<210> SEQ ID NO 136
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(4)
<223> OTHER INFORMATION: L-2,3-diaminopropionic acid
<220> FEATURE:
<221> NAME/KEY: MOD_RES
<222> LOCATION: (5)..(5)
<223> OTHER INFORMATION: D-amino acid
<220> FEATURE:
```

```
<221> NAME/KEY: MOD_RES
<222> LOCATION: (7)..(8)
<223> OTHER INFORMATION: L-2,3-diaminopropionic acid

<400> SEQUENCE: 136

Thr Xaa Xaa Xaa Phe Leu Xaa Xaa Thr
1               5

<210> SEQ ID NO 137
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: L-2-amino-3-guanidinylpropionic acid
<220> FEATURE:
<221> NAME/KEY: MOD_RES
<222> LOCATION: (3)..(3)
<223> OTHER INFORMATION: L-2,3-diaminopropionic acid
<220> FEATURE:
<221> NAME/KEY: MOD_RES
<222> LOCATION: (4)..(4)
<223> OTHER INFORMATION: L-2-amino-3-guanidinylpropionic acid
<220> FEATURE:
<221> NAME/KEY: MOD_RES
<222> LOCATION: (5)..(5)
<223> OTHER INFORMATION: D-phenylalanine
<220> FEATURE:
<221> NAME/KEY: MOD_RES
<222> LOCATION: (7)..(8)
<223> OTHER INFORMATION: L-2-amino-3-guanidinylpropionic acid

<400> SEQUENCE: 137

Thr Xaa Xaa Xaa Phe Leu Xaa Xaa Thr
1               5

<210> SEQ ID NO 138
<211> LENGTH: 29
<212> TYPE: PRT
<213> ORGANISM: Artificial Sequence
<220> FEATURE:
<223> OTHER INFORMATION: synthetic construct

<400> SEQUENCE: 138

Arg Gln Ile Lys Ile Trp Phe Gln Asn Arg Arg Met Lys Trp Lys Lys
1               5                   10                  15

Gly Gly Thr Ala Leu Asp Trp Ser Trp Leu Gln Thr Glu
            20                  25

<210> SEQ ID NO 139
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (5)..(5)
<223> OTHER INFORMATION: L-2,3-diaminopropionic acid
<220> FEATURE:
<221> NAME/KEY: MOD_RES
<222> LOCATION: (7)..(7)
<223> OTHER INFORMATION: L-2-naphthylalanine
<220> FEATURE:
<221> NAME/KEY: MOD_RES
```

```
<222> LOCATION: (11)..(11)
<223> OTHER INFORMATION: L-2,3-diaminopropionic acid
<220> FEATURE:
<221> NAME/KEY: MOD_RES
<222> LOCATION: (12)..(13)
<223> OTHER INFORMATION: L-beta-alanine

<400> SEQUENCE: 139

Gly Trp Ile Tyr Xaa Phe Xaa Arg Arg Arg Xaa Xaa Xaa Lys
1               5                   10

<210> SEQ ID NO 140
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (5)..(5)
<223> OTHER INFORMATION: L-2,3-diaminopropionic acid
<220> FEATURE:
<221> NAME/KEY: MOD_RES
<222> LOCATION: (7)..(7)
<223> OTHER INFORMATION: L-2-naphthylalanine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 140

Gly Trp Ile Tyr Xaa Phe Xaa Arg Arg Arg Xaa Xaa Xaa Lys
1               5                   10                  15

<210> SEQ ID NO 141
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (5)..(5)
<223> OTHER INFORMATION: L-2,3-diaminopropionic acid
<220> FEATURE:
<221> NAME/KEY: MOD_RES
<222> LOCATION: (7)..(7)
<223> OTHER INFORMATION: L-2-naphthylalanine
<220> FEATURE:
<221> NAME/KEY: MOD_RES
<222> LOCATION: (11)..(11)
<223> OTHER INFORMATION: L-2,3-diaminopropionic acid
<220> FEATURE:
<221> NAME/KEY: MOD_RES
<222> LOCATION: (13)..(13)
<223> OTHER INFORMATION: L-beta-alanine

<400> SEQUENCE: 141

Gly Trp Ile Tyr Xaa Phe Xaa Arg Arg Arg Xaa Arg Xaa Lys
1               5                   10
```

```
<210> SEQ ID NO 142
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (5)..(5)
<223> OTHER INFORMATION: L-2,3-diaminopropionic acid
<220> FEATURE:
<221> NAME/KEY: MOD_RES
<222> LOCATION: (7)..(7)
<223> OTHER INFORMATION: L-2-naphthylalanine
<220> FEATURE:
<221> NAME/KEY: MOD_RES
<222> LOCATION: (11)..(11)
<223> OTHER INFORMATION: L-2,3-diaminopropionic acid
<220> FEATURE:
<221> NAME/KEY: MOD_RES
<222> LOCATION: (12)..(12)
<223> OTHER INFORMATION: D-arginine
<220> FEATURE:
<221> NAME/KEY: MOD_RES
<222> LOCATION: (13)..(13)
<223> OTHER INFORMATION: L-beta-alanine

<400> SEQUENCE: 142

Gly Trp Ile Tyr Xaa Phe Xaa Arg Arg Arg Xaa Arg Xaa Lys
1               5                   10

<210> SEQ ID NO 143
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (5)..(5)
<223> OTHER INFORMATION: L-2,3-diaminopropionic acid
<220> FEATURE:
<221> NAME/KEY: MOD_RES
<222> LOCATION: (7)..(7)
<223> OTHER INFORMATION: L-2-naphthylalanine
<220> FEATURE:
<221> NAME/KEY: MOD_RES
<222> LOCATION: (9)..(9)
<223> OTHER INFORMATION: D-arginine
<220> FEATURE:
<221> NAME/KEY: MOD_RES
<222> LOCATION: (11)..(11)
<223> OTHER INFORMATION: L-2,3-diaminopropionic acid
<220> FEATURE:
<221> NAME/KEY: MOD_RES
<222> LOCATION: (12)..(13)
<223> OTHER INFORMATION: L-beta-alanine

<400> SEQUENCE: 143

Gly Trp Ile Tyr Xaa Phe Xaa Arg Arg Arg Xaa Xaa Xaa Lys
1               5                   10

<210> SEQ ID NO 144
<211> LENGTH: 15
<212> TYPE: PRT
<213> ORGANISM: Artificial Sequence
<220> FEATURE:
```

```
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 144

Gly Trp Ile Tyr Ala Xaa Phe Xaa Arg Arg Arg Xaa Xaa Xaa Lys
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 145

Gly Trp Ile Tyr Ala Xaa Phe Xaa Arg Arg Arg Xaa Xaa Xaa Lys
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Alanine is modified with trimesic acid
```

```
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 146

Ala Gly Trp Ile Tyr Xaa Phe Xaa Arg Arg Arg Xaa Xaa Xaa Lys
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Alanine is modified with trimesic acid
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 147

Ala Gly Trp Ile Tyr Xaa Phe Xaa Arg Arg Arg Xaa Xaa Xaa Lys
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Alanine is modified with trimesic acid
<220> FEATURE:
```

```
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 148

Ala Trp Ile Tyr Ala Xaa Phe Xaa Arg Arg Arg Xaa Xaa Xaa Lys
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 149

Gly Ala Ile Tyr Ala Xaa Phe Xaa Arg Arg Arg Xaa Xaa Xaa Lys
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
```

-continued

```
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 150

Gly Trp Ala Tyr Ala Xaa Phe Xaa Arg Arg Arg Xaa Xaa Xaa Lys
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 151

Gly Trp Ile Ala Ala Xaa Phe Xaa Arg Arg Arg Xaa Xaa Xaa Lys
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
```

```
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 152

Gly Trp Ile Tyr Ala Xaa Ala Xaa Arg Arg Arg Xaa Xaa Xaa Lys
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 153

Gly Trp Ile Tyr Ala Xaa Phe Ala Arg Arg Arg Xaa Xaa Xaa Lys
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine
```

-continued

```
<400> SEQUENCE: 154

Gly Trp Ile Tyr Ala Xaa Phe Xaa Ala Arg Arg Xaa Xaa Xaa Lys
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-alanine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 155

Gly Trp Ile Tyr Ala Xaa Phe Xaa Arg Ala Arg Xaa Xaa Xaa Lys
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 156

Gly Trp Ile Tyr Ala Xaa Phe Xaa Arg Arg Ala Xaa Xaa Xaa Lys
1               5                   10                  15
```

```
<210> SEQ ID NO 157
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 157

Gly Ala Ile Ala Ala Xaa Phe Xaa Arg Arg Arg Xaa Xaa Xaa Lys
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Glycine is modified with trimesic acid
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2-naphthylalanine
<220> FEATURE:
<221> NAME/KEY: MOD_RES
<222> LOCATION: (10)..(10)
<223> OTHER INFORMATION: D-arginine
<220> FEATURE:
<221> NAME/KEY: MOD_RES
<222> LOCATION: (12)..(12)
<223> OTHER INFORMATION: L-2,3-diaminopropionic acid
<220> FEATURE:
<221> NAME/KEY: MOD_RES
<222> LOCATION: (13)..(14)
<223> OTHER INFORMATION: L-beta-alanine

<400> SEQUENCE: 158

Gly Ala Ala Ala Ala Xaa Phe Xaa Arg Arg Arg Xaa Xaa Xaa Lys
1               5                   10                  15
```